(12) United States Patent
Rooney et al.

(10) Patent No.: US 8,362,329 B2
(45) Date of Patent: Jan. 29, 2013

(54) INTERGENERIC HYBRID PLANTS AND METHODS FOR PRODUCTION THEREOF

(75) Inventors: William L. Rooney, College Station, TX (US); George L. Hodnett, College Station, TX (US); Leslie C. Kuhlman, Lawrence, KS (US); David M. Stelly, College Station, TX (US); Harold James Price, College Station, TX (US); Patricia K. Price, legal representative, College Station, TX (US)

(73) Assignee: The Texas A&M University System, College Station, TX (US)

( * ) Notice: Subject to any disclaimer, the term of this patent is extended or adjusted under 35 U.S.C. 154(b) by 705 days.

(21) Appl. No.: 12/508,907

(22) Filed: Jul. 24, 2009

(65) Prior Publication Data
US 2010/0050501 A1 Mar. 4, 2010

Related U.S. Application Data

(60) Provisional application No. 61/103,085, filed on Oct. 6, 2008, provisional application No. 61/083,436, filed on Jul. 24, 2008.

(51) Int. Cl.
*A01H 5/00* (2006.01)
*C12N 15/82* (2006.01)
(52) U.S. Cl. ........ 800/320; 800/260; 800/278; 800/275; 435/415
(58) Field of Classification Search ................. None
See application file for complete search history.

(56) References Cited

FOREIGN PATENT DOCUMENTS

| CN | 1802441 A | 7/2006 |
|---|---|---|
| CN | 101037639 A | 9/2007 |
| WO | WO 2004/090171 | 10/2004 |

OTHER PUBLICATIONS

Laurie and Bennett 1989, Annals of Botany 64:675-681.*
Bourne, "A comparative study of certain morphological characters of surgarcane X sorgo hybrids," *J. Agric. Res.*, 50:539-552, 1935.
Bower et al., "High-efficiency, microprojectile-mediated cotransformation of sugarcane, using visible or selectable markers," *Molecular Breeding*, 2:239-249, 1996.
De Wet et al., "Cytogenetics of introgression from saccharum into sorghum," *Crop Sci.*, 16:568-572, 1976.
Gallo-Meagher et al., "Herbicide resistant transgenic sugarcane plants containing the bar gene," *Crop Sci.*, 36:1367-1374, 1996.
Gupta et al., "Morphology of saccharum-sorghum hybrid derivatives," *Amer. J. Bot.*, 65(9):936-942, 1978.
Hodnett et al., "Pollen-pistil interactions result in reproductive isolation between sorghum bicolor and divergent sorghum species," *Crop Sci.*, 45:1403-1409, 2005.
Howe et al., "Rapid and reproducible *Agrobacterium*-mediated transformation of *Sorghum*," *Plant Cell Rep.*, 25:784-791, 2006.
Kuhlman et al., "Genetic recombination of *Sorghum bicolor* x *S. macrospermum* interspecific hybrids," *Genome*, 51:749-756, 2008.
Kuhlman, "Sorghum Introgression Breeding Utilizing *S. macrospermum*," Ph.D. Dissertation, Texas A&M University, Aug. 2007.
Laurie et al., "Genetic variation in *Sorghum* for the inhibition of maize pollen tube growth," *Annals of Botany*, 64:675-681, 1989.
Lo et al., "Breeding of *Saccharum*-miscanthus hybrids for fibre resource," Proceedings XX Congress, pp. 892-898, International Society of Sugar Cane Technologists, Thompson (Ed.), The Organizing Committee of the XX ISSCT Congress, Sao Paulo, Brazil, Oct. 12-21, 1989.
Moriya, "Contributions to the cytology of genus *Saccharum*," In: Cytology vol. 11, Fujii (Ed.) pp. 117-135, Tokyo, 1940-1941.
Nair et al., "Characterization of intergeneric hybrids of *Saccharum* using molecular markers," *Genetic Resources and Crop Evolution*, 53:163-169, 2006.
Nair, "Production and cyto-morphological analysis of intergeneric hybrids of *Sorghum* X *Saccharum*," *Euphytica*, 108:187-191, 1999.
Paterson et al., "Ancient polyploidization predating divergence of the cereals, and its consequences for comparative genomics," *PNAS*, 101(26):9903-9908, 2004.
Price et al., "Genotype dependent interspecific hybridization of *Sorghum bicolor*," *Crop Sci.*, 46:2617-2622, 2006.
Rooney et al., "Designing *sorghum* as a dedicated bioenergy feedstock," *Biofuels, Bioproducts and Biorefining*, 1(2):147-157, 2007.
Terajima et al., "The simultaneous production of sugar and biomass ethanol using high-biomass sugarcane derived from inter-specific and inter-generic cross in Japan," Proceedings of Biomass Asia Workshop 2, Bangkok, Thailand, Dec. 13-15, 2005 (Abstract).
Venkatraman et al., "Sugarcane-*sorghum* hybrids. PI. General outline and early characters," *Ind. J. Agric. Sci.*, 2L:19-27, 1932.
James, "New types of maize X *tripsacum* and maize x *sorghum* hybrids—their use in maize improvement," *Proceedings of the tenth meeting of the Maize and Sorghum Section of Eucarpia, European Assoc. For Res. On Plant Breedings*, Varna, Sep. 17-19, 1979.

* cited by examiner

*Primary Examiner* — Li Zheng
(74) *Attorney, Agent, or Firm* — SNR Denton US LLP

(57) ABSTRACT

Methods for the production of an intergeneric hybrid plants and plants produced thereby. In certain aspects, intergeneric hybrid plants are produced by crossing a *sorghum* parent plant comprising a mutant *sorghum* iap allele with a second moncot plant. Methods for the use of such plants and products obtained therefrom are also provided.

12 Claims, 6 Drawing Sheets

INTERGENERIC HYBRID PLANTS AND METHODS FOR PRODUCTION THEREOF

This application claims priority to U.S. Provisional Application No. 61/103,085, filed on Oct. 6, 2008, and to U.S. Provisional Application No. 61/083,436, filed on Jul. 24, 2008. The foregoing applications are incorporated herein by reference in their entirety.

This invention was made with government support under CSREES National Research Initiative grant number 2004-35300-14686 awarded by the U.S. Department of Agriculture (USDA). The United States government has certain rights in the invention.

BACKGROUND OF THE INVENTION

1. Field of the Invention

The present invention relates generally to the field of plant genetics. More particularly, it concerns intergeneric hybrid plants and methods for production and use thereof.

2. Description of Related Art

By 2025, world energy consumption is expected to increase 57% over 2002 levels. While many different alternative energy sources will be used to meet this demand, it is clear that the production of energy from biomass will be necessary to meet the goals described in the Energy Independence and Security Act of 2007, which requires fuel producers to use at least 36 billion gallons of alternative fuels annually by 2022. Production of alternate fuels from starch alone will not meet these goals. This will require a significant investment in research and an industrial commitment to reach these production goals. The development of this new biofuel industry must be based on the production of dedicated bioenergy feedstocks to insure a consistent and stable biomass supply, thereby justifying the large capital investment needed to build biomass conversion plants. While crop residues from currently grown feed and food crops can and will be used, they will likely only serve to supplement biomass production from dedicated energy crops on an as needed basis.

There thus far has been relatively little emphasis placed on the development and improvement of crops dedicated to biofuel production. Several of the species most commonly proposed as dedicated biofuel feedstocks include switchgrass (*Panicum virgatum*), poplar (*Populus* sp.), sugar/energycane (*Saccharum* sp.), miscanthus (*Miscanthus* sp.), and sorghum (*Sorghum bicolor*). There are now agronomic, breeding, and genomic programs focused on enhancing the cellulosic bioenergy potential of these plant species. However, at present, there is not a given crop species that embodies all of the desired characteristics of a dedicated biofuel feedstock.

SUMMARY OF THE INVENTION

In a first aspect the invention provides an intergeneric plant produced by crossing a *sorghum* parent plant with a monocot plant from a different genus to obtain a progeny therefrom. The *sorghum* parent plant may be homozygous for a recessive *sorghum* iap allele. In certain aspects, for example, the moncot parent plant is a grass, such as a plant in the Poaceae family. For instance, the second monocot parent plant can be a *Saccharum*, *Miscanthus*, a *Saccharum*×*Miscanthus* hybrid, *Erianthus*, *Sorghastrum*, *Panicum*, *Pennisetum* or *Zea* plant. In certain specific embodiments, the second monocot plant is a *Pennisetum purpureum*, *Panicum virgatum*, *Pennisetum ciliare*, *Pennisetum glaucum*, *Andropogon gerardii*, *Andropogon hallii*, *Schizachyrium scoparium*, *Sorghastrum nutans*, *Arundo donax*, *Tripsicum dactyloides*, *Sporobolus airiodes*, *Miscanthus floridulus*, *Miscanthus sinensis*, *Zea mays*, *Zea nicaraguensis*, *Zea perennis* or *Zea diploperennis* plant. In particular aspects, the *sorghum* and/or second parent plant comprises one or more transgenes.

Thus, in one embodiment, the invention provides intergeneric hybrid plants produced from a *sorghum* parent plant. In certain aspects, the *sorghum* parent plant is a *Sorghum bicolor* plant or a hybrid between *Sorghum bicolor* and a wild *sorghum* variety, wherein the plant is homozygous for a recessive *sorghum* iap allele. In further embodiments, the parent *sorghum* plant comprises a male sterility trait, such as a cytoplasmic or genetic male sterility allele (e.g., *sorghum* ms3). In a specific embodiment, the parent *sorghum* plant may be defined as an agronomically elite *sorghum* plant. Those of skill in the art understand that agronomically elite refers to a culmination of distinguishable traits contributing to a beneficial phenotype which allows a producer to harvest a product of commercial significance. Such traits may include yield, vigor, disease resistance, environmental stress tolerance, and pest resistance. In further specific embodiments, the *sorghum* plant may be an agronomically elite *sorghum* plant adapted for biofuel production. In still further embodiments, the parent *sorghum* plant may be a plant of *sorghum* line Tx3361.

In another aspect, the invention provides a part of an intergeneric hybrid plant disclosed herein. A part of an intergeneric hybrid plant includes, but is not limited to, a protoplast, cell, gamete, meristem, root, pistil, anther, flower, seed, embryo, stalk or petiole. In certain aspects, an intergeneric plant seed is provided. In some cases, the intergeneric plant seed may be defined as comprising a functional endosperm. In further aspects, a plant seed may comprise an artificial seed coat comprising a pesticide, a fungicide (see, e.g., U.S. Pat. No. 3,849,934), a nutrient, or a water or temperature-sensitive polymer. In certain aspects, a seed coating comprise an agent to improve seed mechanical handling properties, seed germination, seedling establishment or growth. Processes that may be used for coating of seeds are disclosed, for example, in U.S. Pat. Nos. 2,799,241; 3,089,824; 3,177,027; 3,196,827; 3,207,824; 3,241,520; and 3,253,994, incorporated herein by reference. The skilled artisan will recognize that seed coats may be used, for example, to increase the viability (e.g., percent of seeds that germinates) or the storability of plant seeds. In still further aspects, an intergeneric plant part is provided of a plant comprising a doubled number of *sorghum* chromosomes, such as a plant gamete comprising 2n *sorghum* chromosomes. The skilled worker will recognize that such gametes may, in certain aspects, be produced by treating an intergeneric plant with a microtubule inhibiting agent or chromosome doubling agent, such as a chemical chromosome doubling agent (e.g., colchicine).

In yet another aspect, an intergeneric plant provided herein may be defined as comprising one or more transgenes. For example, an intergeneric plant can comprise a transgene which confers disease resistance, insect resistance, herbicide resistance, drought tolerance, salt tolerance, male sterility, increased biomass or enhanced sugar content. In specific embodiments, the transgene can be directly introduced into the intergeneric hybrid plant. In still further aspects, a transgene may be inherited from a parent plant. The parent plant may have been directly transformed or may have inherited the transgene from a progenitor thereof. In some aspects the invention provides a method involving crossing a parent *sorghum* plant with a second plant wherein parent *sorghum* plant and/or the second comprise a transgene and selecting a progeny plant that comprises the transgene. In certain aspects, a method involving breeding a transgenic plant of the invention may comprise selecting a progeny plant by marker-assisted selection (e.g., by detection of a transgene or product thereof).

In further embodiments, there is provided a progeny plant of an intergeneric hybrid plant described herein. In specific embodiments, the progeny plant is produced by vegetative propagation or by grafting. In some further aspects, a progeny plant may be grown from a seed.

In still further embodiments, there is provided a tissue culture of regenerable cells of an intergeneric plant described herein. The regenerable cells can, in certain aspects, be from embryos, meristematic cells, pollen, leaves, roots, root tips, anther, pistil, flower, seed, boll or stem of an intergeneric plant. Thus, in some aspects, there is provided an intergeneric plant regenerated from a tissue culture regenerable cells.

In yet another embodiment, there is provided a method for producing a commercial product comprising obtaining an intergeneric hybrid plant, or a part thereof, and producing a commercial product therefrom. In certain aspects, the commercial product is defined as a fermentable (e.g., biofuel) feedstock, sucrose juice, bagasse, ethanol, biodiesel, sugar, silage, grain flour or animal feed. In some aspects, the intergeneric hybrid plant is a Sorcane plant and the commercial product is a fermentable (e.g., biofuel) feedstock, Sorcane juice, molasses, bagasse, ethanol, biodiesel, bioplastic or sugar. For example, a fermentable feedstock may be used for producing a biofuel such as ethanol (see, e.g., U.S. Pat. Nos. 5,053,231 and 6,927,048, incorporated herein by reference), biodiesel, chemical (e.g., acetic acid and ammonia) or may be used for gasification. In certain aspects intergeneric hybrid plants or parts thereof may be used as celluosic feedstock. For example, cellulosic material from an intergeneric hybrid may be enzymatically and or chemically digested to free carbohydrates for ethanol fermentation (see, e.g., U.S. Pat. No. 4,355,108, incorporated herein by reference). Any such commercial product therefore forms one part of the invention.

In certain aspects the invention provides a Sorcane juice such as a partially or substantially purified a sugar solution from a Sorcane plant. In certain aspects, a Sorcane juice may be defined as comprising a *sorghum* polynucleotide or polypeptide sequence. For example, a Sorcane juice may be defined as comprising a *sorghum* polynucleotide sequence encoding a recessive *sorghum* iap allele. In a further aspect, the juice may be defined as comprising *sorghum* and *sugarcane* DNA.

In further specific embodiments, a "Sorcane" intergeneric hybrid plant is provided produced by crossing a *sorghum* parent plant with a *Saccharum* (or *Saccharum* hybrid, such as a *Saccharum×miscanthus* plant) parent plant, wherein the *sorghum* parent plant is homozygous for a recessive *sorghum* iap allele. For example, the *sorghum* parent plant may be a *Sorghum bicolor* plant or a hybrid between *Sorghum bicolor* and a wild *sorghum* species. Some examples of *Saccharum* parent plants include, but are not limited to *Saccharum spontaneum, S. officinarum* or a *Saccharum officinarum×Saccharum spontaneum* hybrid plants. In certain specific aspects, a Sorcane plant may be produced as a cross between as *sorghum* parent plant and a L06-024, HoCP05-904 or Ho06-562 variety of *Saccharum* plant.

In yet a further aspect, the invention provides a *sorghum* plant, or part thereof, comprising a male sterility trait wherein the plant is homozygous for a recessive *sorghum* iap allele. For example, the *sorghum* plant may comprise cytoplasmic or genetic male sterility. In some aspects, the *sorghum* plant comprises a *sorghum* ms3 genetic sterility trait. In certain specific aspects, the plant may be a plant of line Tx3361.

In still yet a further aspect, the invention provides a method for producing an intergeneric embryo, the method comprising the steps of: (a) crossing the *sorghum* plant with a second monocot plant which is a species different from *sorghum*, wherein the first *sorghum* plant is homozygous for the *sorghum* iap allele and is used as a female parent; and (b) obtaining an intergeneric hybrid embryo resulting from the crossing. In certain cases the method may further comprise the step of (c) growing the hybrid embryo to produce an intergeneric hybrid plant. In certain aspects, a method provided herein may be defined as a method for producing an intergeneric hybrid plant. In a further aspect, the *sorghum* parent plant for use in methods described here comprises male sterility, such as comprises genetic male sterility or cytoplasmic male sterility.

In still a further aspect, a method of the invention may comprise producing a plurality of intergeneric hybrid plants and selecting an intergeneric hybrid, wherein the intergeneric hybrid comprises characteristics different from either parent. In some embodiments, the method further comprises (d) backcrossing the intergeneric hybrid plant to obtain a monocot plant. In a further embodiment, the method comprises further backcrossing the plant to produce an introgressed progeny plant homozygous for at least one introgressed trait or gene.

In certain aspects, a second parent plant crossed to a *sorghum* plant in accordance with the invention is a plant in the Poaceae family. For example, the second parent plant may be a *Saccharum, Miscanthus*, a *Saccharum×Miscanthus* hybrid, *Erianthus, Sorghastrum, Panicum, Pennisetum* or *Zea* plant. In certain specific embodiments, the second monocot plant is a *Pennisetum purpureum, Pennisetum ciliare, Pennisetum glaucum, Andropogon gerardii, Andropogon hallii, Schizachyrium scoparium, Sorghastrum nutans, Arundo donax, Tripsicum dactyloides, Sporobolus airiodes, Miscanthus floridulus, Miscanthus sinensis, Zea mays, Zea nicaraguensis, Zea perennis* or *Zea diploperennis* plant. In some specific aspects, the second monocot plant may be *Saccharum*, for example, *Saccharum officinarum, Saccharum spontaneum*, or a *Saccharum officinarum×Saccharum spontaneum* hybrid. In some other aspects, the second monocot plant may be a *Miscanthus* plant, such as *Miscanthus sinensis*.

In some aspects, backcrossing may be carried out between an intergeneric hybrid or progeny thereof and a non-*sorghum* parent plant (e.g., a *Andropogoneae* parent plant), a clone thereof or an at least 90% identical plant in terms of bioenergy yield from the same species. In certain other aspects, In some aspects, backcrossing may be carried out between an intergeneric hybrid, or progeny thereof and a *sorghum* parent plant. The backcrossing could be serial backcrossing, such as backcrossing for at least 2 to 10 times.

In certain embodiments, this method may comprise: (i) collecting pollen from the second monocot plant; and (ii) pollinating a flower on the *sorghum* parent plant with the pollen.

In certain aspects, methods for producing an intergeneric embryo as described herein may be further defined as producing a hybrid seed, wherein the seed comprises an embryo and a functional endosperm. In certain other embodiments, a hybrid seed may comprise an embryo and a non-functional endosperm. In one aspect of the invention, embryos (e.g., embryos associated with a non-functional endosperm) may be rescued using tissue culture methods to produce an intergeneric hybrid plant. For example, in some aspects, step (b) further comprises isolating an embryo resulting from the crossing by embryo rescue.

In still further aspects, characteristics for expression in an intergeneric hybrid plant may include biomass yield, improved growth traits or certain desirable trait. Such characteristics may result from heterosis as a result of the particular parent lines selected for hybridization. The characteristic may include, for example, biomass content, fertility, vegetative propagation, photoperiod insensitivity, height, stem diameter, drought resistance, seed size, germination, seed viability after storage, or any other characteristics of interest. For example, biomass content may be improved by altering sucrose content or cellulose content. To compare or quantify biomass yield, standard biomass analytic procedures may be used which are well known to the skilled artisan. Detailed protocols for standard biomass analytic procedures are also freely available from the U.S. National Renewable Energy Laboratory. For example, sucrose or cellulose content may be measured by HPLC or Near Infrared Reflectance spectroscope.

In certain aspects, an intergeneric hybrid plant or seed or F1 progeny may be treated with a chromosome-doubling agent to increase fertility, such as a chemical chromosome doubling agent (e.g., colchicine or a functional equivalent). Treatment of intergeneric hybrid plants with a chromosome doubling agent may be used to generate fertile or partially fertile allopolyploid plants that are capable of self-reproduction. After the treatment, the intergeneric hybrid plant or seed or F1 progeny may be assessed and selected for fertility as a male and/or a female parent.

In a further aspect, the intergeneric hybrid produced from the previous methods may be in the form of a seed or a plant.

In certain embodiments, there is also provided an intergeneric hybrid seed, plant or part thereof produced according to the previous methods. In other aspects, a progeny intergeneric hybrid plant or part thereof clonally propagated from the intergeneric hybrid plant or seed according to the previous methods is also provided. In a further aspect, there is also provided a monocot progeny with the introgressed trait or gene prepared according to the previous methods.

Embodiments discussed in the context of methods and/or compositions of the invention may be employed with respect to any other method or composition described herein. Thus, an embodiment pertaining to one method or composition may be applied to other methods and compositions of the invention as well.

As used herein the term "Sorcane" refers to an intergeneric hybrid between a plant from the *Sorghum* genus and a plant from the *Saccharum* genus (or a hybrid thereof). In certain aspects, a Sorcane plant or plant part may be defined as comprising at least one chromosome or chromosomal segment from the *Sorghum* genus and at least one chromosome or chromosomal segment from the *Saccharum* genus.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, Tx3361 (iap iap) pistil showing maize pollen tube growth, arrow shows maize pollen tube growing through the base of the style into the ovary. FIG. 1B, BTx623 *sorghum* pistil showing no maize pollen tube growth, arrow shows maize pollen tube failing to enter the stigma axis.

FIG. 5A, Two seven-month old *sorghum*×*sugarcane* hybrids. FIG. 5B, An inflorescence of a *sorghum*×*sugarcane* hybrid. FIG. 5C, A mitotic chromosome spread from a *sorghum*×*sugarcane* hybrid.

DESCRIPTION OF ILLUSTRATIVE EMBODIMENTS

Figure 1:
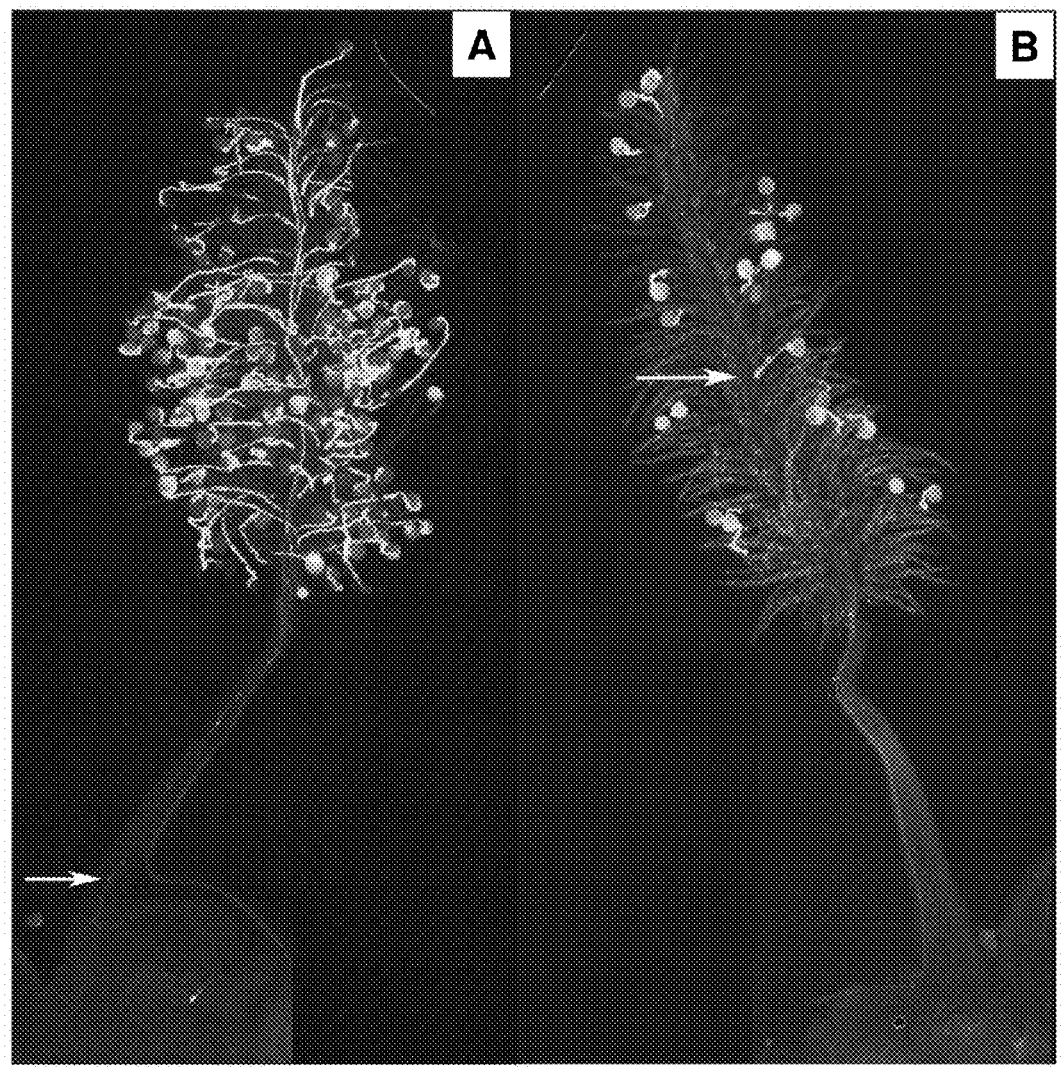
FIG. 1A-B: Effect of iap gene in pollen growth on/in *sorghum* pistils.

Cultivated *sorghum* (*S. bicolor*) has been refractory to traditional plant breeding in that it could not be crossed even with wild, Eu-*sorghum* varieties. The invention overcomes deficiencies in the art by providing, for the first time, efficient methods for producing intergeneric hybrids between *sorghum* and other moncot plants. Intergeneric hybrid plants provided herein comprising unique traits useful in variety of agricultural applications and with particular beneficial traits for the production of biofuels. In certain aspects, the methods described herein allow agronomically important traits to be combined from *sorghum* and a wide array of other monocot plant genera into an intergeneric hybrid plant. Using the methods described herein, agronomically advantageous traits from each parent can be expressed in the hybrid plants, yielding substantially improved traits such as productivity, cold tolerance, drought tolerance, disease tolerance and others.

Studies presented herein demonstrate that *sorghum* plants that are homozygous for the recessive iap allele can be successfully hybridized with moncot plants that include *Saccharum* sp. and *miscanthus*. The hybrid plants produced comprise traits that are distinct from the parent plant varieties. For example, *sorghum*×*Saccharum* "Sorcane" were demonstrated to comprise novel phenotypic characteristics including enhanced sugar content in the stalk.

In certain aspects, intergeneric plants and methods provided herein may be used to engineer advanced feedstock for the production of biofuels. For example, *sugarcane* is a highly preferred biofuel feedstock owing to its high sugar content and unparalleled efficiency in conversion of solar energy into biomass. However, *sugarcane* production is geographically limited to equatorial regions with high rainfall. In temperate dry climates *sorghum* is grown and is contemplated for use as biofuel feedstock, but *sorghum* exhibits far lower sugar content than *sugarcane*. Methods provided herein allow, for the first time, breeding programs capable of combining in a hybrid plant desirable traits from multiple genera including drought tolerance from *sorghum* and sugar production from *Saccharum* to produce an elite biofuel plant.

I. Parent Plants for Producing Intergeneric Hybrids

Certain embodiments of the invention provide methods for producing intergeneric hybrids derived from the cross of a first monocot plant and a second monocot plant which is a different species from the first monocot plant, such as, by crossing a *sugarcane* plant with a *sorghum* plant. In such hybrid crosses, there is a pollen recipient female plant as a parent, as well as a pollen donor male plant as another parent, although it will be recognized that each parent may possess male and female flowers.

In certain aspects, parent plants may be monocot plants. Monocotyledons or monocots are one of two major groups of flowering plants (angiosperms) that are traditionally recognized, the other being dicotyledons or dicots. In a further aspect, parent plants may be *Andropogoneae* plants. *Andropogoneae* is a tribe of grasses (family Poaceae) widespread throughout tropical and temperate regions. They use C4 carbon fixation physiology. This tribe is commonly referred to as the *sorghum* tribe. Genera belonging to this tribe include: *Andropogon, Bothriochloa, Chrysopogon, Coix, Dicanthium* and *Themeda*. Occurrence of this grass is abundant in the tropical savannas of India, Australia, Africa and South America.

*Sorghum, sugarcane* and *miscanthus* as dedicated biofuel feedstocks are related and are representative examples of *Andropogoneae*. Each of these species has relative strengths and potential weaknesses as a biomass feedstock and the ability to move traits between these crops would be extremely valuable for crop improvement programs. Combining the favorable traits from two or three of these might be accomplished by synthesis of a vegetatively heterotic hybrid from two, three or more species, and/or hybridization-based sexual transfer of genes and traits from a donor species to another. Genetic transformation is also a method that might be used to transfer one or a very small number of genes across genera, but contemporary methods do not lend themselves to transferring multigenic agronomic and composition traits that are likely to be of value in biofuel feedstocks. The high cost of regulatory approval for transgenic crops also encourages traditional (sexual) methods of transfer.

To achieve this goal by sexual methods of transfer instead of genetic transformation, it is necessary to overcome interspecific and/or intergeneric reproductive barriers among these grass species. In certain aspects of this invention such reproductive barriers can be circumvented through utilization of a *sorghum* mutant iap gene, thereby providing the potential for combining the most desirable traits from *sorghum, sugarcane* and/or *Miscanthus* species into novel dedicated bioenergy feedstocks to help meet the goals outlined in the Energy Independence and Security Act of 2007.

A. Sorghum

*Sorghum* is widely adapted, drought tolerant and readily propagated via seed. Historically, it has been grown as a feed grain, food grain, and forage worldwide, but varieties and hybrids of energy *sorghums* are being developed that are distinctly different from those used for cereal grain production. Of all the grasses, *sorghum* is unique as a bioenergy crop because hybrids of *sorghum* are available or can be developed that provide high yields of starch (grain hybrids), sugar (sweet *sorghum* cultivars and hybrids), and/or cellulosic biomass (forage and energy *sorghum* hybrids) (Rooney et al., 2007). Because it is already grown from seed as a crop, producers in many regions of the U.S. are familiar with its cultivation, and they have the agricultural infrastructure necessary to grow and harvest the crop. While it is typically grown as an annual crop, it can be ratooned for multiple harvests and is one of the most drought-tolerant and water-use-efficient crops grown (Rooney et al., 2007).

*Sorghum* grain is equally important as a human food in areas outside the United States. In these areas, the grain is consumed in the form of bread, porridge, confectioneries and as an alcoholic beverage Grain *sorghum* may be ground into flour and either used directly or blended with wheat or corn flour in the preparation of food products. In addition to direct consumption of the grain, *sorghum* has long been used in many areas of the world to make beer. The uses of *sorghum*, in addition to human consumption of kernels, include both products of dry- and wet-milling industries. The principle products of *sorghum* dry milling are grits, meal and flour. Starch and other extracts for food use can be provided by the wet milling process.

*Sorghum* provides a source of industrial raw material. Industrial uses are mainly from *sorghum* starch from the wet-milling industry and *sorghum* flour from the dry milling industry. *Sorghum* starch and flour have application in the paper and textile industries. Other industrial uses include applications in adhesives, building materials and as oil-well muds. Considerable amounts of *sorghum*, both grain and plant material, have been used in industrial alcohol production.

*Sorghum* species contemplated in this invention include, but are not limited to, *Sorghum almum, Sorghum amplum, Sorghum angustum, Sorghum arundinaceum, Sorghum bicolor* (primary cultivated species), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum timorense, Sorghum trichocladum, Sorghum versicolor, Sorghum virgatum*, and *Sorghum vulgare*.

One example of *sorghum* used in the present invention is *Sorghum bicolor*. In particular embodiments, an iap/iap mutant *sorghum*, such as those described below may be used. A male sterile iap/iap mutant, including, line Tx3361, which is described in Example 1, may also be used.

In certain aspects, *sorghum* plants described herein may comprise one or more agronomically advantageous traits. These traits may be bred into a parent *sorghum* line and then passed on to an intergeneric hybrid plant or may be bred directly into an intergeneric hybrid line. In certain aspects, agronomically advantageous traits may be introduced by introduction of one or more transgenes into a *sorghum* plant or an intergeneric hybrid plant. In one aspect, a transgene may be introduced into an iap/iap *sorghum* line such as Tx3361 by directly transforming cells from such a *sorghum* plant. In another aspect, a transgene may be introduced into an iap/iap *sorghum* plant by crossing a *sorghum* plant comprising the transgene with an iap/iap *sorghum* line such as Tx3361. $F_1$ progeny from such a cross may then be backcrossed to an iap/iap *sorghum* or self crossed (to other $F_1$ progeny) and the products of the second cross screened for the presence of the transgene and inheritance of a homozygous iap allele. Thus, transgenic *sorghum* plants homozygous for a recessive iap allele are included as part of the invention and may used in methods for producing intergeneric hybrid plants as described herein.

In certain aspects, *sorghum* and intergeneric hybrid plants of the disclosure comprise one or more agronomically advantageous traits including but not limited to increased grain yield, increased sugar content, reduced lodging, reduced stature, drought tolerance, salt tolerance, rust resistance, insect resistance, anthracnose resistance, head smut resistance, downy mildew resistance, gray leaf spot resistance, zonate resistance, leaf burn resistance, virus resistance (e.g., maize dwarf mosaic virus resistance), midge resistance, chinch bug resistance, or green bug resistance. For example plants described herein may comprise a trait for resistance or improved resistance to biotype C and E greenbug (*Schizaphis graminum*), anthracnose (*Colletotricum graminicola*) resistance, resistance to pathotype 1 and 3 downy mildew (*Sclerospora sorghi*) and/or races 1, 2, 3 and 4 of head smut (*Spaoelotheca reiliana*).

B. Sugarcane

Sugarcane or Sugar cane (*Saccharum*) is a genus of 6 to 37 species, depending on taxonomic interpretation, of tall perennial grasses (family Poaceae, tribe *Andropogoneae*) native to warm temperate to tropical regions of the Old World. They have stout, jointed, fibrous stalks that are rich in sugar and generally measure 2 to 6 meters tall. All of the *sugarcane* species interbreed, and the major commercial cultivars are complex hybrids.

Sugarcane is a tropical staple used for the production of crystal sugar. It is also widely used for the production of sugar-derived ethanol in tropical regions of the world and there are numerous other accessions of *sugarcane* that produce even higher biomass, yields but are not as desirable for sugar production. High biomass *sugarcanes* have been designated as energycanes and they have application as a biomass source for cellulosic ethanol production. Sugarcane is unsurpassed for biomass yield potential, but it is a tropical species and adaptation within the U.S. is limited by its susceptibility to cold temperatures. In addition, *sugarcane* requires substantial amounts of water and it is more susceptible to drought than *sorghum*. These factors further limit its production range. Finally, establishment of this perennial crop relies on vegetative propagation which is typically the single most expensive cost throughout the crop's production life.

*Saccharum* (sugarcane) species contemplated in this invention include, but are not necessarily limited to, *Saccharum arundinaceum, Saccharum bengalense, Saccharum brevibarbe, Saccharum edule, Saccharum officinarum, Saccharum procerum, Saccharum ravennae, Saccharum robustum, Saccharum sinense* and *Saccharum spontaneum*. Some *Saccharum* varieties contemplated for use according to the disclosure include but are not limited to *sugarcane* varieties Ho05-961, HB03-403, Ho01-564, Ho05-961, Ho06-525, Ho06-530, Ho06-543, Ho06-552, Ho06-562, Ho06-563, Ho06-565, Ho07-613, Ho95-988, HoCP01-517, HoCP04-803, HoCP04-810, HoCPO04-838, HoCP05-903, HoCP05-904, HoCP05-923, HoCP06-502, HoCP96-540, HoL05-953, L01-283, L06-001, L06-024, L06-38, LCP85-384, US02-840, TCP00-4521, TCP01-4535, TCP02-4622, TCP03-4636, TCP03-4645, MPTH97-209, US07-9014, US079026, US079025, L97-128 (U.S. Plant Pat. No. PP17,636), L99-226 (U.S. Plant Pat. No. PP18,807) and L99-233 (U.S. Plant Pat. No. PP18,826). In certain aspects, a parent *Saccharum* plant may comprise one or more transgenes. For example, a parent *Saccharum* plant may have inherited a transgene from a progenitor plant or may have been directly transformed with a DNA coding for a transgene.

In certain aspects, *Saccharum* plants described herein may comprise one or more agronomically advantageous traits. For example, a Saccharum plant for use herein may be a transgenic *Saccharum* plant comprising a transgene that confers herbicide tolerance (e.g., glyphosate tolerance) or insect resistance (e.g., resistance to the *sugarcane* borer (*Diatreae saccharalis*)).

C. Miscanthus

The genus *Miscanthus* possesses several species that have potential as a cultivated bioenergy feedstock. *Miscanthus* is a genus of about 15 species of perennial grasses native to subtropical and tropical regions of Africa and southern Asia, with one species (*M. sinensis*) extending north into temperate eastern Asia. Examples of species include, but are not necessarily limited to, *Miscanthus floridulus, Miscanthus giganteus, Miscanthus sacchariflorus* (Amur silver-grass), *Miscanthus sinensis, Miscanthus tinctorius* and *Miscanthus transmorrisonensis*.

The rapid growth, low mineral content and high biomass yield of *Miscanthus* make it a favorite choice as a biofuel. After harvest, it can be burned to produce heat and steam for power turbines. The resulting $CO_2$ emissions are equal to the amount of $CO_2$ that the plant collected from the atmosphere during its growing phase, and thus the process is greenhouse gas-neutral, if one does not consider inputs (e.g., fertilizer) or transportation of the biofuel to the point of use. When mixed in a 50/50 mixture with coal, it can be used in some current coal-burning power plants without modifications.

The most prolific of these types is "Giant Miscanthus", a natural interspecific triploid sterile hybrid of *M. sinesis* (diploid) and *M. sacchariflorus* (tetraploid), which must be vegetatively propagated, e.g., with rhizome cuttings or in vitro culture. Specific types of *miscanthus* (such as Giant Miscanthus) produce high yields of biomass, are perennial and adaptable to temperate climates (Clifton-Brown et al., 2001). Commercial viability on a large scale remains unproven, or at least unpublished.

Further plant species and varieties contemplated for use according to this disclosure include *Miscanthus sinensis* (Chinese silver grass, Eulalia grass, Maiden grass, Zebra grass, Porcupine Grass; syn. *Eulalia japonica* Trin., *Miscant-*

*hus sinensis* f. *glaber* Honda, *Miscanthus sinensis* var. *gracillimus* Hitchc., *Miscanthus sinensis* var. *variegatus* Beal, *Miscanthus sinensis* var. *zebrinus* Beal, *Saccharum japonicum* Thunb.), a grass native to eastern Asia throughout most of China, Japan and Korea. It is a herbaceous perennial plant generally growing to 0.8-2 m (rarely 4 m) tall, forming dense clumps from an underground rhizome. The leaves are 18-75 cm long and 0.3-2 cm broad. The flowers are purplish, held above the foliage.

D. Additional Monocots

Additional monocot plants can be used to generate intergeneric crosses as described herein. For example in certain aspects an intergeneric cross is between a *sorghum* and a second monocot of the Poaceae (grass) family. For example a cross can be made between a *sorghum* plant a member of the Anomochlooideae, Pharoideae, (e.g., Pharus and Leptaspis), Puelioideae, Pooideae (e.g., wheat, barley, oats, brome-grass reed-grasses), Bambusoideae (e.g., bamboo), Ehrhartoideae (e.g., rice), Arundinoideae, Centothecoideae, Chloridoideae, Panicoideae (e.g., maize) Micrairoideae or Danthonioideae subfamily of plants. In certain aspects intergeneric plants may be used to introgress desirable traits into a predominantly *sorghum* genetic background. Conversely, in certain cases, intergeneric crosses described here can be used to introgress desirable traits for *sorghum* into other distantly related plant varieties. Some specific intergeneric crosses and intergeneric plants include but are not limited to *sorghum* crosses with genotypes of *Erianthus* sp., *Sorghastrum* sp., *Panicum* sp., *Pennisetum* sp. and *Zea mays*.

In certain aspects a monocot plant used for crosses descried herein may itself be an intergeneric hybrid plant. For example, *sorghum* may be crossed with a Sorcane plant or a miscane plant (*Miscanthus*×*Saccharum*).

II. Use of Pollen-Incompatibility Systems

To achieve the goal of developing efficient and highly productive biofuel feedstock, certain aspects of the present invention provide methods for combining many of the desirable traits present in related species, such as *sorghum*, *sugarcane* and *miscanthus*. In certain aspects, the role of iap in interspecific and intergeneric compatibility is utilized to create hybrids to circumvent reproductive barriers.

A. Self Incompatibility

In certain aspects, self incompatibility can be utilized to minimize selfing or pollination with pollen from the same species. Fertilization is a complex interaction between pollen and pistil that successfully culminates in fusion of male and female nuclei (de Nettancourt, 1997; Swanson et al., 2004; Wheeler et al., 2001). The female pistil tissue provides distinct cues and essential nutrients that support pollen tube growth through several cellular environments (Swanson et al., 2004). At the same time, the pistil presents an elaborate barrier that shields ovules from access to inappropriate pollen, including inter- or intra-species pollination.

The study of self-incompatibility (SI) in flowering plants has advanced to a detailed understanding of S-gene sequences, gene products and gene product interactions (de Nettancourt, 1997; Feng et al., 2006; McClure and Franklin-Tong, 2006; Rahman et al., 2007; Tabah et al., 2004). SI is usually controlled by a single-multiallelic locus, S, which consists of at least two, closely linked genes encoding the pollen and pistil determinants of self-recognition. In recent years, much progress has been made in identifying the female determinants of SI. Most gametophytic SI systems have an S-RNase as the pistil S-component, while a unique gametophytic system has a small secreted peptide as the pistil component (Feng et al., 2006; McClure and Franklin-Tong, 2006). In sporophytic forms of SI, the pistil determinant is an S-receptor kinase, consisting of a conserved kinase domain, a transmembrane domain and a variable extracellular receptor (Naithani et al., 2007; Nasrallah and Nasrallah, 1993; Nasrallah, 2002). The spatial and temporal expression of these genes in reproductive tissues has allowed a detailed account of the cellular and molecular processes that lead to the recognition and rejection of self-incompatible pollen.

B. Cross Incompatibility

For intergeneric crossing the problem of cross incompatibility between different species must be solved. Two main paradigms exist for understanding interspecific cross incompatibility: incompatibility and incongruity. Incompatibility is a mechanism that through the inhibiting action of incompatibility genes, the reproductive relationship is nonfunctional. Incompatibility relies on active rejection of pollen identified as "foreign," similar to the SI system described above. Alternatively, incongruity does not rely on active rejection of pollen but is essentially a passive process in which non-functioning occurs due to a lack of genetic information about one of the partners. An incongruous relationship exists when the male partner lacks a penetrative mechanism to overcome a certain barrier that exists in the female. Species that evolve in isolation from one another are more likely to be incongruent partners due to evolutionary divergence (Hogenboom, 1973). Regardless of the mechanism involved, barriers to interspecific hybridization are common in crop species and overcoming them is a prerequisite for utilizing interspecific or intergeneric crosses in germplasm development programs.

C. Iap Locus in *Sorghum*

Hybridization barriers are present in the genus *Sorghum* and numerous unsuccessful attempts at obtaining hybrids between *S. bicolor* and wild *sorghum* species as well as plants that are more distantly related. An allele that regulates pollen tube growth in female *sorghum* plants has been identified designated Iap. A recessive mutant version of the gene (the iap allele) has also been identified.

The locus for an iap has been localized to the short arm of *sorghum* linkage group 02 (SBI-02) and the locus is flanked with several AFLP and microsatellite markers. The two closest microsatellite markers flanking the iap locus (Xtxp50 and Xtxp63) have been cross referenced to a sequenced-based, high density *sorghum* genome map (see, e.g., sorgblast3.tamu.edu on the web site of Texas A&M University, published in Menz et al., 2002). The regional recombination frequencies (kbp per cM; genes per cM) have been estimated across the genome. It is predicted that the region spanning this iap locus has a regional recombination frequency of ~165 kb/cM. Thus, it is inferred that this Iap trait locus has been delimited to a relatively small segment, ~800 kbp-1 Mbp.

III. Intergeneric Hybrids and Introgression Involving *Sorghum*

The present invention provides methods of intergeneric hybridization and production of biofuel involving introducing desirable traits into a hybrid or a plant species.

A. Production of the Intergeneric Hybrid

The transfer of complex traits between species requires the successful production of inter-specific or inter-generic hybrids. While there are numerous reports in the literature of rare hybridization between *sorghum* and *Saccharum*, and between *Saccharum* and *Miscanthus*, there are no known previous reports of hybridization between *Miscanthus* and *sorghum*. The ability of these species to rarely hybridize is likely related to their genetic similarities, e.g., *sorghum* and *sugarcane* diverged only 5 million years ago (Paterson et al., 2004). DNA sequences of *sorghum*, *Saccharum*, and *Miscanthus* remain very similar today (FIG. 1 in Matthews et al., 2002). However, viable hybrids have been observed only rarely, less than <1 in 1,000 attempts, reflecting their taxonomic and genetic distinctiveness. Such extreme difficulty has eliminated any practical utility for these efforts.

In contrast the invention provides a method allowing the efficient production of intergeneric hybrids. In one aspect, such a method comprising the steps of: (a) obtaining a *sorghum* plant which is homozygous for recessive iap (inhibition of alien pollen gene); (b) crossing the *sorghum* plant with an *Andropogoneae* plant other than a *sorghum* and obtaining an F1 progeny, wherein the *sorghum* plant is used as a female parent and the non-*sorghum Andropogoneae* plant is used as a male parent; and (c) selecting an intergeneric hybrid from the F1 progeny, wherein the intergeneric hybrid has a higher bioenergy yield than either parent.

In crosses carried out in accordance with the invention, in certain cases, it may be desirable to use embryo rescue following pollinating to obtain viable intergeneric hybrid plants, as described herein above, as mature seeds resulting from the intergeneric hybrid crosses have in some cases been found by the inventor to have low rates of viability. It may also be desired to manipulate the photoperiod and/or other growth conditions of the parent plants in order to ensure synchronization of viable pollen and pollen-receptive flowers on the respective parent plants. Advantageously, during this stage, plants may be treated with fertilizer and/or other agricultural chemicals as considered appropriate.

Once an intergeneric cross is made, it is important to identify resulting progeny as hybrid and not simply the result of selfing or pollination with pollen from another plant of the same species. One method for identification is morphological evaluation, provided that the intergeneric hybrid has sufficient distinguishing characteristics, as is the case here. In particular, the characteristics described herein allow one of skill in the art to identify a plant as an intergeneric hybrid plant based on the physical characteristics of the plant derived from each parent plant.

However, other techniques may also find use with the invention and may avoid potential errors caused by environmental variation. For all F1 progeny plants possible, ploidy, chromosome constitution and variation across plants may be determined, as well as genotypic constitution and consistency or variation across plants for a set of parental polymorphic molecular markers from diverse genome locations. For example, in certain aspects, intergeneric progeny may be screened to identify progeny that produce a high percentage of functional 2n gametophytes. These progeny in particular may be useful for breeding and backcrosses for introgression of specific traits.

For example, where parents differ in genome size, flow cytometric or other measurement of DNA content may detect hybrids at early developmental stages. However, since differences in DNA content may be due to reasons other than hybrid status, additional methods of analysis may be desired. As soon as root tips are developed, karyotype analysis can be performed, provided that the parental complements differ in size, number and/or morphology. Other alternatives include use of genomic in situ hybridization (GISH) (Schwarzacher et al., 1989) or genetic marker analysis.

Genetic markers represent an efficient method for analysis and identification of interspecific hybrid plants, and in particular, the combination of genetic complements from different monocot parental plants. As used herein, the phrase "genetic complement" means an aggregate of nucleotide sequences which defines the identity of a plant or a cell of that plant. By way of example, the intergeneric hybrid provided herein could be genotyped to determine a representative sample of the inherited markers it possesses relative to exemplary *sorghum* and *sugarcane/Miscanthus* parent plants.

Genetic markers are alleles at a single locus. They are preferably inherited in codominant fashion so that the presence of both alleles at a diploid locus is readily detectable, and they are free of environmental variation, i.e., their heritability is 1. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence or size of a repeated sequence. Heterozygosity refers to different conditions of the gene at a locus.

A useful type of genetic marker is simple sequence repeats (SSRs), in that they are generally highly polymorphic and inexpensive to score. However, potentially any other type of genetic marker could be used, for example, restriction fragment length polymorphisms (RFLPs), amplified fragment length polymorphisms (AFLPs), single nucleotide polymorphisms (SNPs), and isozymes, to identify a plant of the invention.

In certain aspects, it may be desirable to determine traits of the progeny including fertility, vegetative propagation and biofuel attributes for some or all of the F1 progeny, depending on results from the above determination: if all F1s seem similar, analyze a representative set of F1 plants; if F1 plants vary, then analyze many F1 plant individually as clones. In a further aspect, such progeny or clones may be selected for the desired trait(s), such as improved bioenergy yield compared with either parent.

B. Introgression

Introgression involves the movement of a gene (gene flow) from one species into the gene pool of another by backcrossing. In one embodiment of the invention an interspecific hybrid may be backcrossed with one of its parents. This can permit introgression of one or more traits into the parent, particularly introducing new traits into the species. Introgression is a long-term process; it may take many hybrid generations before the backcrossing occurs. An introgression line (abbreviation: IL) refers to a line of a crop species that contains genetic material derived from a similar species, for example a "wild" relative. Introgression lines allow the study of quantitative trait loci, but also the creation of new varieties by introducing exotic traits.

In certain embodiments of the invention, there may also be provided methods for improving bioenergy yield of a non-*sorghum Andropogoneae* plant, the method comprising the steps of: (a) obtaining a *sorghum* parent which is homozygous for recessive iap; (b) crossing the *sorghum* plant with an *Andropogoneae* plant other than a *sorghum* and obtaining an F1 progeny, wherein the *sorghum* plant is used as a female parent and the non-*sorghum Andropogoneae* plant is used as a male parent; (c) selecting an intergeneric hybrid from the F1 progeny, wherein the intergeneric hybrid has a higher bioenergy yield compared with the non-*sorghum Andropogoneae* plant; and (d) backcrossing the intergeneric hybrid with the non-*sorghum Andropogoneae* plant to obtain an *Andropogoneae* progeny, wherein the *Andropogoneae* progeny has the higher bioenergy yield. In certain embodiments, this method may further comprise: (e) inbreeding the Andropogoneae progeny to produce a second progeny homozygous for the higher bioenergy yield.

C. Selection of Improved Bioenergy Yield

In some aspects, intergeneric hybridization or introgression may be used in the present invention to improve bioenergy yield of certain plants. Selection of higher bioenergy yield can be carried out using standard biomass analytical yield procedures, such as those provided by the U.S. National Renewable Energy Laboratory or similar procedures adopted by The American Society for Testing and Materials and the Technical Association of the Pulp and Paper Industry.

In certain aspects, biomass yield may also include biomass content, fertility, vegetative propagation, photoperiod insensitivity, height, stem diameter, drought resistance, seed size, germination, seed viability after storage, or any characteristics commonly known in the art. For example, biomass content may be sucrose content or cellulose content. In particular, sucrose or cellulose content may be measured by HPLC or Near Infrared Reflectance spectroscope.

D. Herbicide Resistance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al., (1988).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricinacetyl transferase (bar) genes) may also be used. See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European application No. 0 242 246 to Leemans et al., DeGreef et al., (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acct-S1, Accl-S2 and Acct-S3 genes described by Marshall et al., (1992).

Genes are also known conferring resistance to a herbicide that inhibits photosynthesis, such as a triazine (psbA and gs+ genes) and a benzonitrile (nitrilase gene). Przibilla et al., (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., (1992).

E. Disease Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., (1994) (cloning of the tomato Cf-9 gene for resistance to *Cladosporium fulvum*); Martin et al., (1993) (tomato Pto gene for resistance to *Pseudomonas syringae* pv. *tomato*); and Mindrinos et al., (1994) (*Arabidopsis* RPS2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al., (1993), who show that transgenic plants expressing recombinant antibody genes are protected from virus attack.

Logemann et al., (1992), for example, disclose transgenic plants expressing a barley ribosome-inactivating gene have an increased resistance to fungal disease.

F. Insect Resistance

One example of an insect resistance gene includes a *Bacillus thuringiensis* protein, a derivative thereof or a synthetic polypeptide modeled thereon. See, for example, Geiser et al., (1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (1994), who disclose the nucleotide sequences of several *Clivia miniata* mannose-binding lectin genes. A vitamin-binding protein may also be used, such as avidin. See PCT application US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., (1987) (nucleotide sequence of rice cysteine proteinase inhibitor), Huub et al., (1993) (nucleotide sequence of cDNA encoding tobacco proteinase inhibitor I), and Sumitani et al., (1993) (nucleotide sequence of *Streptomyces nitrosporeus* α-amylase inhibitor). An insect-specific hormone or pheromone may also be used. See, for example, the disclosure by Hammock et al., (1990), of baculovirus expression of cloned juvenile hormone esterase, an inactivator of juvenile hormone.

Still other examples include an insect-specific antibody, an immunotoxin derived therefrom, a developmental-arrestive protein or an enzyme. See Taylor et al., (1994), who described enzymatic inactivation in transgenic tobacco via production of single-chain antibody fragments. In further example, a chitinase such as rice chitnase (chi II) may be expressed in a plant (see, e.g., Zhu et al., 1998 and Krishnaveni et al., 2001 which disclose expression of chi II in *sorghum* under the control of a CaMV 35S promoter).

G. Modified Fatty Acid, Phytate and Carbohydrate Metabolism

Genes may be used conferring modified fatty acid metabolism. For example, stearyl-ACP desaturase genes may be used. See Knutzon et al., (1992). Various fatty acid desaturases have also been described, such as a *Saccharomyces cerevisiae* OLE1 gene encoding Δ9 fatty acid desaturase, an enzyme which forms the monounsaturated palmitoleic (16:1) and oleic (18:1) fatty acids from palmitoyl (16:0) or stearoyl (18:0) CoA (McDonough et al., 1992); a gene encoding a stearoyl-acyl carrier protein delta-9 desaturase from castor (Fox et al., 1993); Δ6- and Δ12-desaturases from the cyanobacteria *Synechocystis* responsible for the conversion of linoleic acid (18:2) to gamma-linolenic acid (18:3 gamma) (Reddy et al., 1993); a gene from *Arabidopsis thaliana* that encodes an omega-3 desaturase (Arondel et al., 1992)); plant Δ9-desaturases (PCT Application Publ. No. WO 91/13972) and soybean and *Brassica* Δ15 desaturases (European Patent Application Publ. No. EP 0616644).

Phytate metabolism may also be modified by introduction of a phytase-encoding gene to enhance breakdown of phytate, adding more free phosphate to the transformed plant. For example, see Van Hartingsveldt et al., (1993), for a disclosure of the nucleotide sequence of an *Aspergillus niger* phytase gene. This, for example, could be accomplished by cloning and then reintroducing DNA associated with the single allele which is responsible for plant mutants characterized by low levels of phytic acid. See Raboy et al., (1990).

A number of genes are known that may be used to alter carbohydrate metabolism. For example, plants may be transformed with a gene coding for an enzyme that alters the branching pattern of starch. See Shiroza et al., (1988) (nucleotide sequence of *Streptococcus mutans fructosyltransferase* gene), Steinmetz et al., (1985) (nucleotide sequence of *Bacillus subtilis levansucrase* gene), Pen et al., (1992) (production of transgenic plants that express *Bacillus licheniformis* α-amylase), Elliot et al., (1993) (nucleotide sequences of tomato invertase genes), Sergaard et al., (1993) (site-directed mutagenesis of barley α-amylase gene), and Fisher et al., (1993) (maize endosperm starch branching enzyme II). The Z10 gene encoding a 10 kD zein storage protein from maize may also be used to alter the quantities of 10 kD zein in the cells relative to other components (Kirihara et al., 1988).

H. Further Agronomic Traits

Additional transgenes may be introduced, for example to increase drought or cold tolerance. For example, wax synthetic enzymes may be expressed to increase surface wax content and drought tolerance of hybrid plants. Transgenes that are useful for conferring cold tolerance are disclosed, for example, in U.S. Patent Publication 20080092255, incorporated herein by reference. Additional genes that may be expressed or overexpressed in transgenic plants to improve abiotic stress tolerance include a mannitol-1-phosphate dehydrogenase (e.g., mtlD), a pyrroline-5-carboxylate synthase (e.g., p5CSfl29A), and/or a choline oxidase (e.g., codA).

Commercial traits can also be encoded on a gene or genes which could increase for example, starch for ethanol production, or provide expression of proteins. Another important commercial use of transformed plants is the production of polymers and bioplastics, such as described in U.S. Pat. No. 5,602,321, incorporated herein by reference. Genes such as, B-ketothiolase, PHBase (polyhydroxyburyrate synthase) and acetoacetyl-CoA reductase facilitate expression of polyhyroxyalkanoates (PHAs).

IV. Male Sterility

In certain aspects, hybridization between different but closely related species involves use of *sorghum* iap/iap mutants as a female parent. Because *sorghum* will outcross naturally at low frequencies, special manipulations will generally be desired to make controlled crosses between desired patents (Rooney, 2004). Certain embodiments of the present invention use a male-sterile *sorghum* mutant, for example, Tx 3361 to circumvent the need for hand emasculation. Examples of male sterility are described below.

A. Hand Emasculation

The removal or destruction of viability of male (pollen) parts of a plant, largely for controlled pollination and breeding purposes is called emasculation. Hand emasculation and other methods for control of *sorghum* self-pollination are well known.

Flowers may be emasculated the day before anthesis. Such florets occur below and within about 3 cm of opened florets in a *sorghum* panicle. All open spikelets are removed with scissors. Panicles and equipment should be washed to remove any pollen prior to emasculation, especially if the emasculation occurs outdoors. There is less likely to be such pollen movement in greenhouses, but such rinsing of panicles and equipment should be conducted to avoid unwanted outcrossing.

All florets except those that are to be emasculated are removed, leaving only the florets that are expected to open the next day. The three anthers are coaxed out of the enclosing lemma and palea by inserting a sharpened pencil or similar pointed instrument. Care must be taken not to break the anthers, and if the anther is breached, that flower should be removed and instruments rinsed to avoid contaminating the next floret. Every anther must be removed before the set of florets is "completely emasculated." The presence of one anther will cause pollination of one or more ovaries prior to the transfer of pollen by the breeder. After the florets are emasculated, a paper bag is placed over the emasculated panicle until the florets are pollinated 1-2 days later. Field emasculation usually is carried out during the afternoon in an attempt to avoid stray, viable pollen from other plants.

B. Genetic Male Sterility

A series of nuclear recessive male sterility genes, designated as ms1 through ms7, have been characterized in *sorghum*. In the recessive condition, these mutations result in a male-sterile plant that can be used for hybridization (Rooney, 2001). Because these plants are completely male sterile, there is no need to emasculate, so larger numbers of seed can be made more easily. However, the inability to produce true-breeding, uniform genetic steriles complicates the use of genetic male sterility for hybrid seed production. Consequently, genetic male sterility may be used in *sorghum*-breeding programs in accordance with the invention to facilitate develop intergeneric hybrid plants and the parents thereof.

The use of genetic male sterility facilitates hybridization, but it also requires close management of the population during anthesis. Once improvement is completed, lines must be derived and the recessive ms alleles eliminated or they will produce sterile progeny in future generations. Lines segregating for genetic male sterility can be maintained by self-pollination of random panicles or bulk pollination of sterile panicles with pollen from heterozygous and male-fertile plants in the same row. To use this system, male sterile plants must be identified at tip flowering. Anthers in male-sterile plants are smaller, thinner, and do not shed viable pollen. Upon identification, the tip of the male-sterile panicle should be removed and the panicle bagged to avoid open pollination. The panicle can then be pollinated 3-5 days later with pollen collected from the desired male parent. Hybrids from these crosses can be used for population improvement or to begin another plant-breeding scheme, such as pedigree selection for producing improved pure lines. Breeders have developed genetic male sterility stocks in many elite *sorghum* germplasms and parental lines (Pedersen and Toy 1997).

C. Gametocides

In certain embodiments, emasculation can be achieved using a gametocide to sterilize pollen as desired. Plants treated with such gametocides are rendered male sterile, but typically remain female fertile. The use of chemical gametocides is described, for example, in U.S. Pat. No. 4,936,904, the disclosure of which is specifically incorporated herein by reference in it entirety.

V. Plant Transformation Constructs

In accordance with the invention plants are provided comprising one or more transgene(s) produced by genetic transformation. Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al., (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Examples of components that may be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. The PAL2 promoter may also be useful with the invention (U.S. Pat. Appl. Pub. 2004/0049802, the entire disclosure of which is specifically incorporated herein by reference).

The DNA sequence between the transcription initiation site and the start of the coding sequence, i.e., the untranslated leader sequence, can also influence gene expression. One may thus wish to employ a particular leader sequence with a transformation construct of the invention. Leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable" markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228). The gene that encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

V. Deposit Information

A deposit of the *sorghum* line Tx3361, which is disclosed herein, was made with the American Type Culture Collection (ATCC), 10801 University Blvd., Manassas, Va. 20110-2209. The date of deposit was Jun. 25, 2009 and the accession number for those deposited seeds of *sorghum* variety Tx3361 is ATCC Accession No. PTA-10149. All restrictions upon the deposit have been removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period. Applicants do not waive any patent rights to the deposited materials.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Development of an Improved *Sorghum* Line with the iap iap Genotype

A reproductive barrier exists to production of hybrids between cultivated *sorghum* and other, wild, *sorghum* species (Hodnett et al., 2005). The barrier is prezygotic, as pollen tubes of wild *sorghum* species cease growth in pistils of *sorghum* before reaching and fertilizing the egg (Price et al., 2006).

A single gene locus, designated as Iap (Inhibition of Alien Pollen), is one cause of reproductive isolation between cultivated *sorghum* (*Sorghum bicolor* L. Moench) and wild *sorghum* species outside the Eu-*Sorghum* section. In the homozygous recessive condition, the iap iap genotype eliminates this reproductive isolation and allows hybrids to be recovered between *S. bicolor* and wild *sorghum* relatives (Hodnett et al., 2005; Price et al., 2006). A genotype was first identified in *S. bicolor* accession 'NR481' (Laurie and Bennett, 1989), but this accession has very undesirable agronomic characteristics such as tall height, pigmented testa, and extreme susceptibility to lodging. Its potential for use in an introgression program is limited as any wild species genetic variation recovered in introgression progeny will be in a poor genetic background.

An improved *S. bicolor* germplasm with the iap iap genotype was developed with significantly improved agronomic performance as well as segregation of the ms3 genetic male-sterility system. This line was developed from a cross between genetic male-sterile BTx623, a derivative of BTx623 containing the ms3 allele for genetic male-sterility, and NR481, a line homozygous for the iap allele. The hybrid was backcrossed once to the BTx623 ms3 parent. Fertile BC1F1 progeny were self pollinated and selected for 3-dwarf height, white pericarp, no awns, absence of pigmented testa, and reduced lodging in College Station, Tex. 2005. BC1F2 progeny were grown in a greenhouse, hand emasculated and tested for maize pollen tube growth (Laurie and Bennett, 1989). Genotypes at the Iap locus were based on qualitatively measuring maize pollen tube growth to the base of the style in *sorghum* pistils 24 hours after pollination. Individuals that show maize pollen tube growth to the base of the style are considered iap iap (FIG. 1). Selected iap iap individuals were self pollinated and progeny rows were grown the following season in College Station, Tex. Lines were evaluated for lodging, height, awns, and segregation of the ms3 allele. Selected male-fertile and sterile plants (BC1F3) within ms3 segregating rows were sib-mated. Individual sib crosses were grown in Weslaco, Tex. and evaluated for stable backcross segregation of ms3, lodging, height, maturity, and maize pollen tube growth was used to confirm their Iap locus genotype (Tables 1 and 2). The selected line was bulk sib-mated between male-sterile and fertile plants to produce breeder's seed of the proposed genetic stock. The selected line is a maintainer of sterility in the A1 cytoplasmic male sterility system.

The observed expression of the iap iap genotype, maize pollen tube growth to the base of the style, was at a lower frequency than previously reported (Laurie and Bennett, 1989) and is likely environmentally influenced. Tx3361 had expression similar to NR481 in all tested environments. This genetic stock can be used as a female parent to obtain interspecific crosses with exotic *sorghum* species and possibly species beyond the genus. Any recovered introgression will be in a more favorable genetic background for further evaluation and breeding.

TABLE 1

Agronomic traits of the two parents and the proposed genetic stock evaluated in Weslaco, TX 2006

|  | NR481 | BTx623ms3 | Tx3361 | LSD $_{(.05)}$ |
|---|---|---|---|---|
| Dwarf Loci[1] | dw2[†] | dw1 Dw2 dw3 dw4 | dw1 Dw2 dw3 dw4 |  |
| Pericarp Color[2] | R | W | W |  |
| Awns[3] | Y | N | N |  |
| Pigmented Testa[3] | Y | N | N |  |
| ms3 backcross segregation[3] | N | Y | Y |  |
| Maize PTG[4] | 22.5%[A] | 0.0%[B] | 15.3%[A] | 11.0% |
| Iap Locus | iap iap | Iap Iap | iap iap |  |
| Height (in.) | 92[A] | 54[B] | 54[B] | 7.5 |
| Exsertion (in.) | 8.3[A] | 3.6[B] | 4.5[B] | 2.8 |
| Lodging[5] | 5.7[A] | 0.6[B] | 1.8[B] | 1.5 |
| Days to 50% Anthesis | 49[C] | 65[A] | 53[B] | 3.5 |

[1]Dwarf Loci: represents the homozygous allele at each dwarfing locus;
[†]NR481 has 2 loci that are homozygous recessive but only the genotype at Dw2 is known;
[2]Pericarp color: R = red, W = white;
[3]Awns, pigmented testa, and ms3 backcross segregation: Y = yes, N = no;
[4]Frequency of *sorghum* pistils with maize pollen tube growth to the base of the style. Values are means, different letters within rows indicate significantly different means a = .05;
[5]Lodging: 0-9 scale, 0 = 0-10%, 9 = 90-100% lodging The Tx3361 line was selected, evaluated, and increased in the Texas AGRILIFE™ Research *sorghum* breeding program at College Station, Tex. Using the numbering system of the AGRILIFE™ *sorghum* improvement program, this genetic stock was designated as Tx3361. The Tx3361 line was the subject of a phenotypic evaluation, the results of which are presented in Table 2 below.

TABLE 2

Physiological and Morphological Traits for Sorghum Line Tx3361

| CHARACTERISTIC | Tx3361 |
|---|---|
| 1. General |  |
| Kind | *sorghum* |
| Type | Germplasm segregating for ms3 |
| Cytoplasm and Restorer Status | Maintainer in A1, A2 and A3 |
| Use Class | Grain |
| 2. Maturity |  |
| Days from Planting to Mid- | 63 |
| Number of Days Earlier Than | 7 |
| 3. Plant |  |
| Coleoptile | Green |
| Plant Pigment | Purple |
| 4. Stalk |  |
| Diameter | Mid-Stout |
| 5. Stalk Height |  |
| cm From Soil to Top of Plant | 112 |
| cm Greater Than RTx437 | 25 |
| No. of Recessive Height Genes | 3 |
| Plant Height Genotype | dw1 Dw2 dw3 dw4 |
| Waxy Bloom | Present |
| Tillers | Moderate |
| Sweetness | Insipid |
| Juiciness | Dry (Pithy) |
| Panicle Exsertion | Medium |
| Degree of Senescence | Intermediate |
| 6. Leaf |  |
| Width (Relative to Class) | Moderate |
| Color | Dark Green |
| Margin | Smooth |
| Attitude | Horizontal |
| Ligule | Present |
| Midrib Color | White |
| 7. Panicle |  |
| Anther Color (At Flowering) | Light Yellow |
| cm Panicle Length | 30 |
| cm Greater Than RTx437 | 5 |
| Density | Semi-Open |
| Shape | Oval |

TABLE 2-continued

Physiological and Morphological Traits for Sorghum Line Tx3361

| CHARACTERISTIC | Tx3361 |
|---|---|
| Length of Central Rachis (% of Rachis Branches (At Grain Rachis Branch Average Glumes | 75% Horizontal Intermediate |
| Length | Intermediate |
| % of Grain Covered by | 25% |
| Texture | Intermediate |
| Color (At Grain Maturity) | Light Tan |
| Hairiness | Smooth |
| Venation | Present |
| Transverse Wrinkle | Absent |
| Awns | Absent |
| 8. Roots | |
| Roots | Fibrous |
| 9. Grain | |
| Testa | Absent |
| Mesocarp Thickness | Thick |
| Epicarp Color (Genetic) | White |
| Grain Color (Appearance) | White Chalky (Opaque) |
| Endosperm Color | White |
| Endosperm Type | Starchy |
| Endosperm Texture | Intermediate |
| Seed Shape | Oval |
| 10. Insect Resistance | |
| Sorghum Midge | Susceptible |

*These are typical values. Values may vary due to environment.

Example 2

Production Intergeneric Hybrids with Sorghum Parent Line Tx3361 ms3

In the fall of 2007, Tx3361ms3 plants were pollinated with pollen from *Saccharum spontaneum*, commercial *sugarcane* (*S. officinarum×S. spontaneum*), and *miscane* (*Miscanthus× Saccharum*).

Figure 2:
FIG. 2: *Sorghum*×*Saccharum* hybrid plant, germinated from a planted seed.

The Tx3361 ms3×*sugarcane* crosses were successful and over 1500 putative F1 seeds were harvested (produced on a total of 17 plants that were pollinated). Twenty-six putative F1 hybrid seedlings (produced from 75 seeds) were planted and an exemplary plant is shown in FIG. 2.

Pollinations of Tx3361 ms3×*S. spontaneum* and Tx3361ms3×*M. sinesis* were successful, as fertilization occurred and embryos were formed, but development was typically hindered by endosperm breakdown. In the Tx3361 ms3×*miscane* hybrids, embryo rescue was successful and 16 putative hybrids have been recovered. Therefore, in cases when endosperm breakdown occurs, in vitro culture of embryos was found to be effective to recover F1 hybrids.

In all of these hybrids, the utilization of mutant iap in Tx3361 ms3 was crucial as pollinations with normal (homozygous Iap) Tx623 ms3 have never shown evidence of fertilization, embryo or endosperm development.

Figure 3:
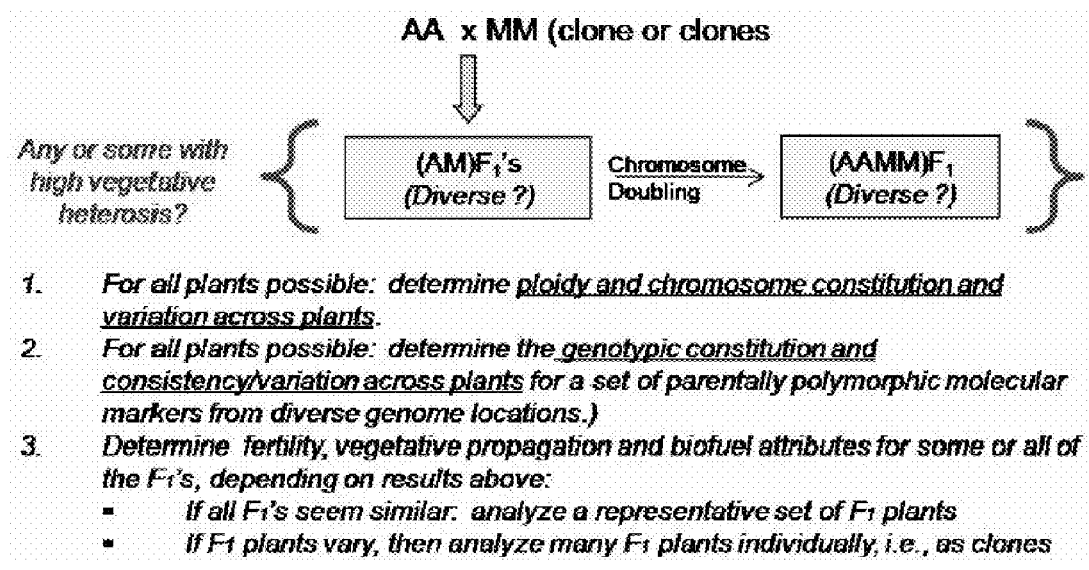
FIG. 3: Schematic representing the direct use of intergeneric hybrids. The designation AA refers to *sorghum* while MM refers to the pollinator genera, e.g., *miscanthus, sugarcane*.
Figure 4:
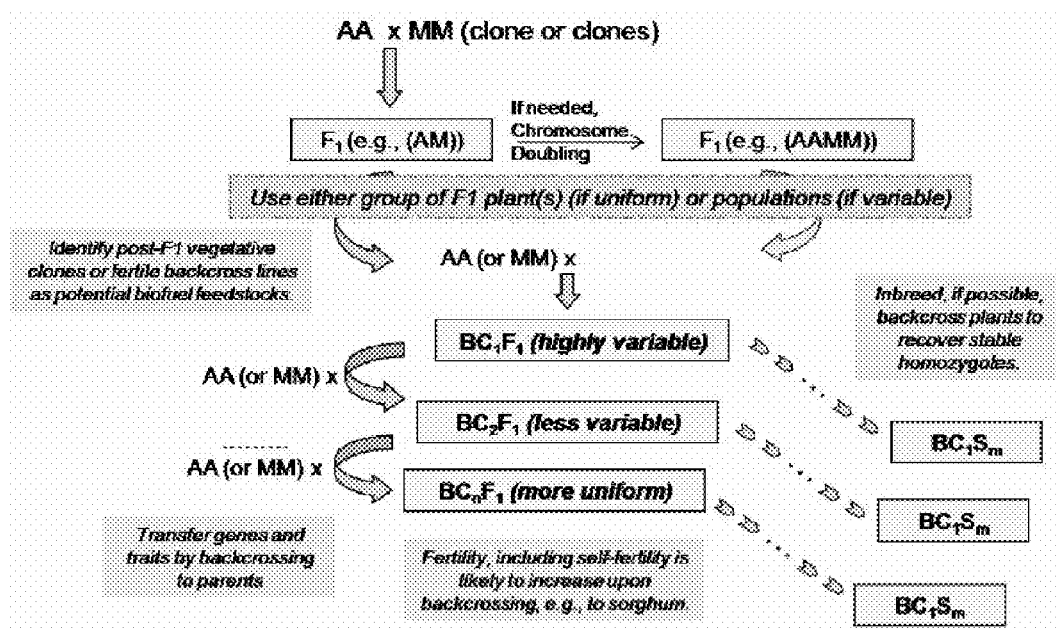
FIG. 4: Schematic representing the indirect (introgression) use of intergeneric hybrids. The designation AA refers to *sorghum* while MM refers to the pollinator genera, e.g., *miscanthus, sugarcane*.

In 2008, numerous hybrids of *sorghum×sugarcane* and *sorghum×miscane* were produced and grown in the greenhouse. Numerous *sorghum×M. sinesis* embryos were also produced. These plants did not exhibit a phenotype that resembles Tx3361, the seed parent. The intergeneric hybrids have potential to be used directly, either as seed or clonally propagated biofuel crops or as a means of introgressing genes and traits from one species to another. Exemplary protocols for introgression are illustrated in FIGS. 3 and 4.

Example 3

Production and Analysis of *Sorghum×Sugarcane* Hybrids

Seed of line Tx3361 was planted in pots in the greenhouse from mid-July through mid-September so that anthesis would match with *sugarcane* anthesis. At the onset of anthesis, male sterile plants of Tx3361 were identified and bagged based on anther phenotype. *Sorghum×sugarcane* pollinations were made at the USDA-ARS *Sugarcane* Research Unit in Houma, La. between late September and early November of 2007 and 2008. Additional pollinations were made in College Station, in January and February. A total of 67 basic and commercial *sugarcane* breeding lines were used as male parents.

Pollinations made in Houma were completed by dusting the *sorghum* panicle with *sugarcane* pollen and rubbing the *sorghum* panicle through the *sugarcane* tassel. In the following year, crosses were made by placing one to three *sorghum* panicles with a single *sugarcane* parent and tapping the *sugarcane* tassels followed by rubbing the *sorghum* panicles into the *sugarcane* tassels. This process was repeated for three or four consecutive days. Upon completion of these crosses, pollinated *sorghum* plants were returned to College Station for seed development and maturation. For the *sorghum×sugarcane* crosses made in College Station each *sorghum* panicle was pollinated one time; pollinations were made using the same methodology practiced in Houma in the prior year.

Seed Preparation

Seeds were removed from the maternal parent on average at 46, 41, and 27 days post pollination over three years respectively. Seed from the first year were stored from 30 to 90 d prior to germination while seed from the following years were germinated immediately after harvest. The timeline for harvest and germination was decreased due to the high frequency of vivipary in the seed. After harvest and prior to germination, seeds were surface sterilized by first coating them with a liquid suspension of Captan and Apron for at least half an hour and then immersing them in a 30% solution of bleach for 20 minutes. After surface sterilization the seeds were rinsed in sterile water and placed embryo side up in a petri dish containing a culture medium of Murashige-Skoog (Murashige and Skoog, 1962) basal salts and vitamins supplemented with 10 mg L-1 glycine, 10 mg L-1 L-arginine-HCl, 10 mg L-1 L-tyrosine, 100 mg L-1 inositol, and 30 g L-1 sucrose, solidified with 0.7% agar (plant tissue culture grade, Phytotechnology Laboratories, Shawnee Mission, Kans.) (Sharma, 1999). All petri dishes were sealed with Parafilm and placed under grow lights set to 14 hour days with a constant temperature between 27 and 30° C. All seeds that showed good development in both the root and shoot were potted in 4" pots. Once established, they were transferred to the greenhouse.

Confirmation of Intergeneric Hybrid Plants

Intergeneric hybrids were initially classified by morphology. As they developed, all hybrids exhibited numerous characteristics of *sugarcane* (height, tillering, maturity) that the maternal parent did not possess, in addition to having traits not passed by the paternal parent. These plants were confirmed as intergeneric hybrids by somatic chromosome number. Chromosome spreads were prepared from root tips using a method described by Jewell and Islam-Faridi (1994) with the following modifications. Young actively growing root tips were pretreated with a saturated aqueous solution of α-bromonaphthalene for 2.75 h at room temperature and fixed overnight in 3:1 95% ethanol/glacial acetic acid (3:1 v/v). Root tips were then rinsed several times with distilled water, hydrolyzed for 10 min in 0.2 M HCl and rinsed 10 min in distilled water. Cell walls were digested with an aqueous solution of 5% cellulase (Onozuka R-10, Yakult Honsha Co. Ltd., Tokyo) and 1.0% pectolyase Y-23 (Seishin Corporation, Tokyo) at pH 4.5 for 35 to 60 min at 37° C. and rinsed three times with distilled water. Meristems were placed on a clean glass slide in an ethanol/glacial acetic acid (3:1) solution, macerated, and spread with fine-tipped forceps, air-dried at room temperature for 2 d, and stained with Azure Blue. Root tip spreads were examined using a Zeiss Universal II microscope (Carl Zeiss Inc., Gottingen, Germany) with 63× and 100× apochromat objectives. Images were captured with an Optronics VI-470 system (Optronics Inc., Goleta, Calif.) and digitally stored and processed with Optimas (v. 6.1) image analysis software (Optimas Corp., Bothell, Wash.).

Effect of *Sugarcane* Pollinator on Hybrid Seed Set

For each cross made in Houma in the second year, the *sugarcane* parent, date of pollination, location of pollination, pollen load, florets/panicle, seeds/panicle and seedlings produced were recorded. *Sugarcane* pollen load was a subjective measurement determined at the time hybrid seed was harvested by evaluating the dried stigmas under a dissecting scope and rating them as light, medium or heavy; light meant little or no pollen observable; medium rank was assigned if pollen was observed on a number of the stigmas while a heavy rank was assigned if thorough coverage was observed. For each cross made in College Station in the third year the *sugarcane* parent, date of pollination, seeds/panicle and seedlings produced were recorded.

To determine relative effect of location, date of pollination and *sugarcane* pollinator on seed set and pollen load, PROC GLM in SAS v9.1 was used. Only *sugarcane* males that had been used in at least three pollinations were included in the analysis. All effects were considered fixed and only interactions involving the pollinator were included in the analysis of variance.

2007 Hybrid Seed Production, Confirmation and Growth

In the fall of 2007 (first year), a total of 24 pollinations were made using 17 different pollinators (Table 3). Based on stigma reaction, it was apparent that fertilization had occurred after pollination. Seed began to develop, although size and rate of growth was reduced compared to normal *sorghum* self or cross-pollination. When the seed was prepared for germination (after harvest and storage), it was evident embryo loss during seed development and vivipary after development was common; further analysis revealed that 32% were viviparous and 39% had no embryo. A fair proportion of the remaining seed germinated and produced plants. All of these plants were intergeneric hybrids and they reflected a wide range of phenotypes, from very poor in growth to highly vigorous.

Figure 5:
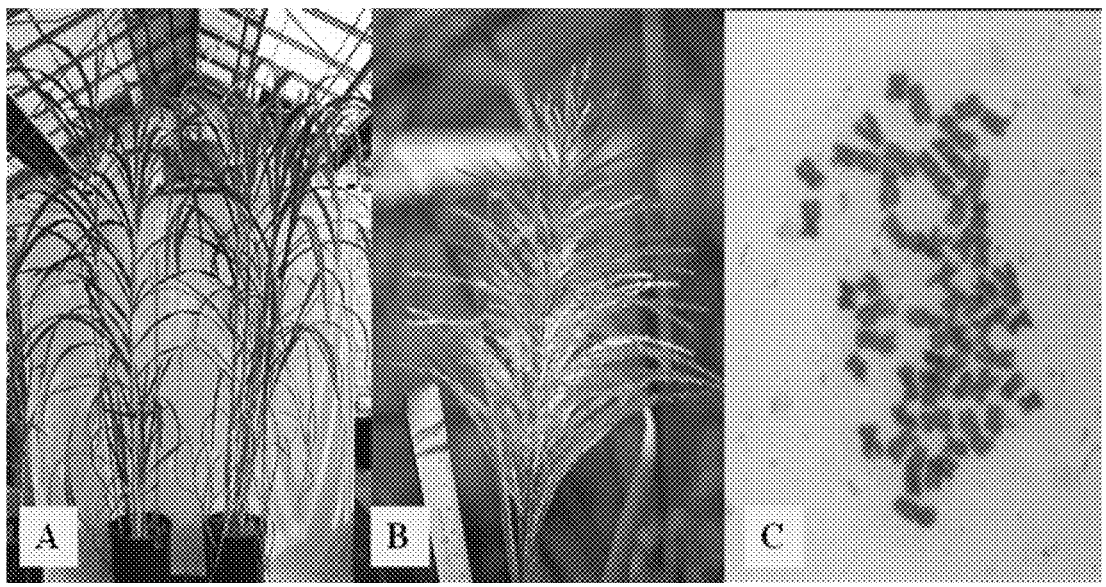
FIG. 5A-C: Photographs of *sorghum*×*sugarcane* intergeneric hybrids grown in College Station, Tex.
Figure 6:
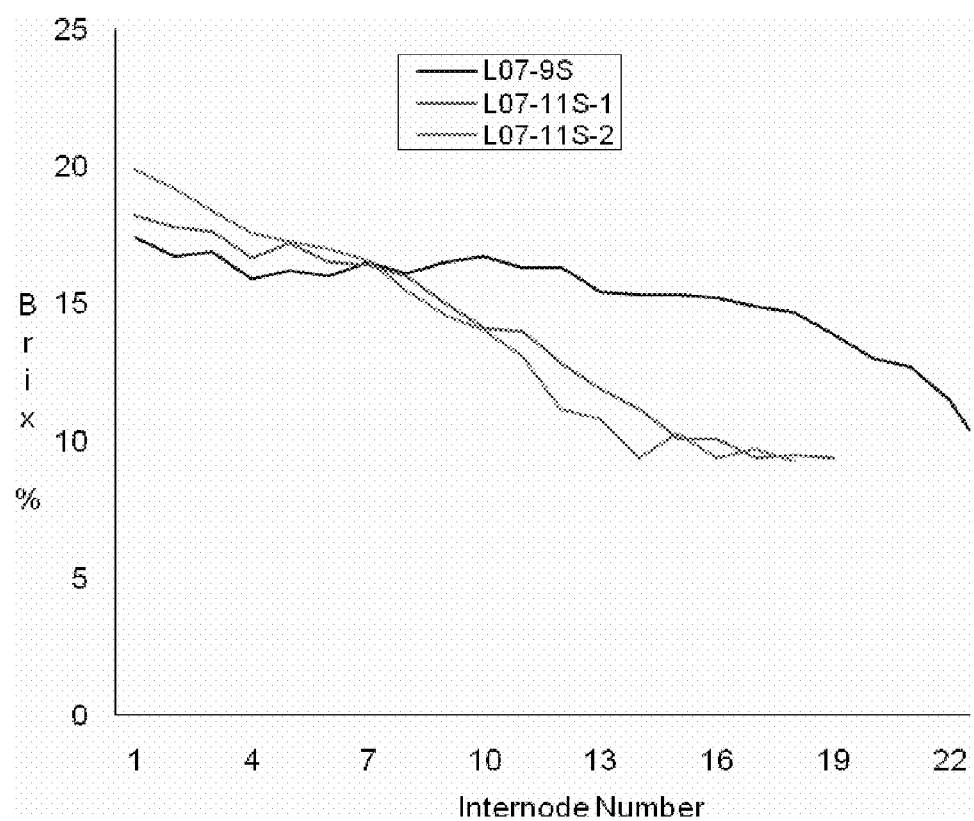
FIG. 6: Brix measurement (total solubles in juice as measured by refractometer) based on location of the internode on the plant. Internode 1 was located at the base of the plant; highest numbers are at the top of the plant. The sugar profiles in these plants were measured in August when the plants were approximately eight months old and had not yet entered into reproductive growth.

From these pollinations, 23 of the best hybrids were transplanted into pots in the greenhouse. All of these plants had morphological features similar to *sugarcane* (FIG. 5). Somatic chromosome counts for these hybrids ranged from 56 to 64; 10 chromosomes were from *sorghum* and the rest of the chromosomes were from *Saccharum*. The hybrids have long narrow and numerous leaves compared to Tx3361, which has fewer leaves that are shorter and broader. Upon development the 23 hybrids displayed a wide range of vigor and growth habit; two of these hybrids displayed excellent growth and development. These hybrids were vigorous and tillered much like *sugarcane* although each had morphological traits unique to *sorghum* such as nodal brace roots and/or excessive waxy bloom on leaf sheaths. In seven months, canes of hybrid L07-11S were 3.1 m while canes of hybrid L07-9S were 2.7 m (FIG. 5A). Both of these hybrids were photoperiod sensitive like *sugarcane*, flowering from mid December through January in College Station whereas Tx3361 flowers in approximately 65 d regardless of planting date. The panicles on these hybrids were slightly more compact than those of *sugarcane*; attempts to testcross confirmed both male and female sterility of these two particular hybrids. In August, several canes of both hybrids were cut to test for vegetative propagation and sugar distribution. Vegetative propagation was successful and sugar concentration in these hybrids was similar to the pattern found in *sugarcane* with increasing sugar concentrations in the more mature internodes (FIG. 6) (Whittaker and Botha, 1997).

Further Hybrid Seed Production and Enhancement of Process (2008/2009)

In 2008 a total of 155 *sorghum* panicles (totaling 74,300 florets) were pollinated. From these pollinations, 10,347 seed were recovered, resulting in an average seed set of 14%. Percent seed set was not measured in the 2009 pollinations, but it appeared similar to that observed in 2008. However germination was substantially improved between the 2008 and 2009 pollinations because seed was harvested earlier and losses due to vivipary were avoided. In 2009, germination increased from 2008 to 2009 because seed were harvested earlier (28 days post pollination versus 40 days post pollination) to avoid losses due to vivipary. In addition, 2008 germination was further reduced by the embryo's inability to grow through the seed coat; hence, in all of the 2009 seed the pericarp was removed prior to plating on media. As the technique improved, germination rates improved from 2.5% in 2007 to 5.7% in 2008 to 33% in 2009.

TABLE 3

Sugarcane Parents Used in the *Sorghum* × Sugarcane Crosses

| Male | Panicles | Florets | Seed no. | Seedlings | Field Test |
|---|---|---|---|---|---|
| Houma Pollinators 2007 | | | | | |
| Example 2007 Males | | | | | |
| Ho00-961 | 1 | | 4 | 1 | |
| HoCP01-517 | 1 | | 8 | 1 | |
| HoCP04-838 | 1 | | 59 | 2 | 1 |
| HoCP96-540 | 1 | | 46 | 2 | |
| 2007 Totals | 24 | | 1504 | 23 | 2 |
| Houma Pollinators 2008 | | | | | |
| Example 2008 Males | | | | | |
| Erianthus | 1 | 544 | 0 | 0 | 0 |
| Ho01-564 | 5 | 3,275 | 334 | 16 | 1 |
| Ho05-961 | 23 | 8,976 | 1,691 | 160 | 88 |
| Ho06-525 | 6 | 2,765 | 301 | 19 | 10 |
| Ho06-530 | 1 | 975 | 0 | 0 | 0 |
| Ho06-543 | 2 | 592 | 9 | 1 | 0 |
| Ho06-552 | 2 | 978 | 10 | 0 | 1 |
| Ho06-562 | 4 | 1,725 | 480 | 13 | 0 |
| Ho06-563 | 1 | 281 | 85 | 3 | 2 |
| Ho06-565 | 2 | 408 | 199 | 0 | 0 |
| Ho07-613 | 2 | 1,131 | 316 | 1 | 0 |
| Ho95-988 | 1 | 760 | 43 | 0 | 0 |
| HoCP01-517 | 5 | 2,506 | 217 | 14 | 5 |
| HoCP04-803 | 1 | 393 | 19 | 1 | 0 |
| HoCP04-810 | 2 | 1,120 | 10 | 0 | 0 |
| HoCP04-838 | 8 | 5,152 | 603 | 91 | 46 |
| HoCP05-903 | 2 | 894 | 72 | 0 | 0 |
| HoCP05-904 | 3 | 2,074 | 581 | 34 | 19 |

TABLE 3-continued

Sugarcane Parents Used in the *Sorghum* × Sugarcane Crosses

| Male | Panicles | Florets | Seed no. | Seedlings | Field Test |
|---|---|---|---|---|---|
| HoCP05-923 | 3 | 951 | 4 | 2 | 0 |
| HoCP06-502 | 1 | 159 | 13 | 0 | 0 |
| HoCP96-540 | 11 | 6,934 | 929 | 86 | 12 |
| HoL05-953 | 1 | 240 | 22 | 0 | 0 |
| L01-283 | 9 | 4,972 | 1,301 | 36 | 7 |
| L06-001 | 1 | 795 | 31 | 3 | 0 |
| L06-024 | 3 | 1,260 | 669 | 40 | 16 |
| L06-38 | 2 | 872 | 32 | 0 | 0 |
| L99-226 | 2 | 592 | 5 | 1 | 0 |
| L99-266 | 1 | 475 | 90 | 21 | 2 |
| LCP85-384 | 3 | 1,937 | 145 | 11 | 3 |
| US02-840 | 1 | 557 | 2 | 0 | 0 |
| 2008 Totals | 155 | 74,743 | 10,347 | 592 | 217 |
| Texas Pollinators 2009 | | | | | |
| TCP00-4521 | 16 | | 28 | 9 | 5 |
| TCP01-4535 | 7 | | 66 | 32 | 13 |
| TCP02-4622 | 11 | | 362 | 128 | 23 |
| TCP03-4636 | 30 | | 1,651 | 519 | 215 |
| TCP03-4645 | 9 | | 203 | 68 | 12 |
| Total | 73 | | 2,310 | 756 | 268 |
| Grand Total | 252 | 74,743 | 14,161 | 1371 | 487 |

From the combined 2008/2009 pollinations, a total of 1348 seedlings were potted and transferred to the greenhouse. The phenotypic variation present in these hybrids was extensive, but all were morphologically more like *sugarcane* than *sorghum*. In the spring of 2009, 485 hybrids were selected (based on vigor) and transplanted into a space-plant nursery near College Station (Table 3). These hybrids are expected to follow growth and development patterns observed in the limited set of hybrids evaluated from the 2007 crosses.

Effect of Pollinator Parent on Seed Set and Germination

Analysis of variance detected a significant effect on seed set due to pollinator parent (Table 4). The range of variation due to pollinator clearly indicates that certain *sugarcane* varieties are better pollinators for the production of intergeneric hybrids on Tx3361. *Sugarcane* pollinators such as L06-024, HoCP05-904 and Ho06-562 demonstrate the most effective hybrid seed production (Table 5).

TABLE 4

Analysis of variance for seed set and pollen load for seventeen sugarcane pollinators used to pollinate Tx3361 in Houma, La in the fall of 2008

| Source | Seed Set | | | Pollen Load | | |
|---|---|---|---|---|---|---|
| | df | MS | Pr > F | df | MS | Pr > F |
| Location | 3 | 0.031 | 0.216 | 3 | 0.655 | 0.093 |
| Date(Location) | 14 | 0.025 | 0.283 | 15 | 0.631 | 0.019 |
| Male | 16 | 0.047 | 0.010 | 16 | 0.877 | 0.001 |
| Male* Location | 10 | 0.022 | 0.381 | 10 | 0.285 | 0.474 |
| Male*Date(Location) | 8 | 0.031 | 0.167 | 9 | 0.739 | 0.016 |
| Error | | | | | | |

TABLE 5

Number of pollinations, Percent seed set on Tx3361 and pollinator pollen load for 17 different sugarcane cultivars and/or breeding lines in the fall of 2008 in Houma, La.

| Sugarcane Pollinator* | Pollinations -----no.----- | Seed set ---%--- | Pollen load** |
|---|---|---|---|
| L06-024 | 3 | 53.0 | 2.33 |
| HoCP05-904 | 3 | 36.0 | 2.67 |
| Ho06-562 | 4 | 25.2 | 2.50 |
| L01-283 | 9 | 24.9 | 2.00 |
| Ho05-961 | 23 | 18.2 | 1.65 |
| HB03-403 | 5 | 15.6 | 1.80 |
| HoCP04-838 | 8 | 15.3 | 2.10 |
| HoCP96-540 | 11 | 13.6 | 1.64 |
| HoCP01-517 | 5 | 10.1 | 1.40 |
| Ho01-564 | 5 | 8.9 | 1.40 |
| Ho06-525 | 5 | 8.6 | 1.80 |
| MPTH97-209 | 4 | 8.2 | 2.00 |
| LCP85-384 | 3 | 7.5 | 3.00 |
| US07-9014 | 7 | 5.7 | 1.86 |
| US079026 | 7 | 0.7 | 1.00 |
| US079025 | 3 | 0.6 | 1.67 |
| HoCP05-923 | 3 | 0.4 | 1.00 |
| Mean | | 14.8 | 1.80 |
| L.S.D. | | 18.5 | 0.70 |

*Only pollinators that were used in at least three pollinations were included in this analysis;
**Pollen load rating were 1 (light), 2 (medium) and 3 (heavy).

It has been known that pollen shed in *sugarcane* is influenced by genotype and environment (Moore and Nuss, 1987) and analysis of variance confirmed that pollen load was influenced by pollinator parent as well as date of pollination (Table 4). Lines with low pollen load consistently produced crosses with low seed set, but high pollen load did not necessarily indicate a high seed set. Six of the top seven *sugarcane* pollinators (defined by seed set percentage) had average or above average pollen load while males with below average seed set varied in pollen load (Table 5). These results imply that males must not only produce good pollen but that they must also have favorable genetic and/or genomic compatibility with Tx3361.

Analysis of variance of 2009 data indicated that neither pollination environment nor *sugarcane* pollinator influenced percent germination. Based on the current technology for managing seed production and germination, it is reasonable to expect between 25-40% of those seed to germinate and produce plants regardless of which pollinator is used and where the pollination is made.

Example 4

Pollen Tube Growth in *Sorghum* Wide Hybrids

In view of the successful hybridizations demonstrated herein, Tx3361 *sorghum* plants were further pollinated with pollen from additional genera of plants. Following pollination pollen tube growth was observed and recorded (Table 6). Values in the column labeled style indicate the amount of pollen tube growth, with higher values indicating the most growth.

TABLE 6

Pollen tube growth in *sorghum* wide crosses

| Species | Common | Assession | Pistils | Pollen Grains | Germination | Stigma | Axis | Style γ 4 | γ 2 | Base | Ovary |
|---|---|---|---|---|---|---|---|---|---|---|---|
| *Pennisetum purpureum* | elephant grass | PI-410307 | | | | | | | | | |
| *Pennisetum purpureum* | elephant grass | PI-410305 | 24 | Pollen count too numerous, Moderate growth in stigmas, very minimal growth in stigma axis | | | | | | | |
| *Pennisetum ciliare* | buffel grass | Frio | 58 | 346 | 264 | 114 | 49 | 20 | 10 | 8 | 8 |
| *Pennisetum ciliare* | buffel grass | Common | 12 | >1800 | >1200 | >1000 | >240 | 86 | 82 | 74 | 61 |
| *Pennisetum glaucum* | pearl millet | PI-286837 | 24 | 790 | 600 | 137 | 5 | 0 | 0 | 0 | 0 |
| *Pennisetum glaucum* | pearl millet | PI-164410 | 22 | 1661 | 1431 | 564 | 3 | 1 | 0 | 0 | 0 |
| *Pennisetum glaucum* | pearl millet | PI213011 | | | | | | | | | |
| *Andropogon gerardii* | big bluestem | PI-315661 | | | | | | | | | |
| *Andropogon gerardii* | big bluestem | PI-483446 | | | | | | | | | |
| *Andropogon gerardii* | big bluestem | PI-635103 | | | | | | | | | |
| *Andropogon hallii* | sand bluestem | PI-421277 | | | | | | | | | |
| *Andropogon hallii* | sand bluestem | PI-477974 | | | | | | | | | |
| *Andropogon hallii* | sand bluestem | PI-648358 | | | | | | | | | |
| *Schizachyrium scoparium* | little bluestem | PI-216758 | | | | | | | | | |
| *Schizachyrium scoparium* | little bluestem | PI-635105 | | | | | | | | | |
| *Schizachyrium scoparium* | little bluestem | PI-648371 | | | | | | | | | |
| *Sorghastrum nutans* | indian grass | 476279 | 20 | >2202 | 1276 | 711 | 185 | 3 | 1 | 0 | 0 |
| *Sorghastrum nutans* | indian grass | 47699 | 47 | >2388 | 560 | 119 | 17 | 8 | 5 | 0 | 0 |
| *Arundo donax* | giant reed | CS | | | | | | | | | |
| *Arundo donax* | giant reed | Navasota | | | | | | | | | |
| *Tripsicum dactyloides* | gamma grass | PI-421612 | | | | | | | | | |
| *Tripsicum dactyloides* | gamma grass | PI-585050 | | | | | | | | | |
| *Tripsicum dactyloides* | gamma grass | PI-595898 | | | | | | | | | |
| *Sporobolus airiodes* | alkali sacaton | PI-241072 | | | | | | | | | |
| *Sporobolus airiodes* | alkali sacaton | PI-33068 | | | | | | | | | |
| *Sporobolus airiodes* | alkali sacaton | PI-434445 | | | | | | | | | |
| *Miscanthus floridulus* | giant miscanthus | PI-230189 | 13 | 1366 | 1150 | 926 | 495 | 64 | 19 | 6 | 0 |
| *Miscanthus floridulus* | giant miscanthus | CANE-3908 | | | | | | | | | |
| *Miscanthus sinensis* | chinese plumegrass | PI-295764 | 11 | >1570 | >1563 | >1052 | >130 | >98 | 22 | 3 | 0 |
| *Miscanthus sinensis* | chinese plumegrass | CANE 9233 | 23 | 645 | 511 | 299 | 147 | 88 | 33 | 1 | 0 |
| *Miscanthus sinensis* | chinese plumegrass | PI-294605 | | | | | | | | | |
| *Miscanthus sinensis* | chinese plumegrass | PI-294602 | 21 | >777 | >687 | >438 | >180 | >68 | 16 | 0 | 0 |
| *Zea mays* var. Kandy Korn | sweet corn | | 33 | >1572 | >1567 | >955 | >111 | 69 | 66 | 60 | 26 |
| *Zea mays* var. Tender Treat | sweet corn | | 12 | 314 | 292 | 186 | 54 | 0 | 0 | 0 | 0 |
| *Zea mays* var. Silver Queen | sweet corn | | 9 | 586 | 529 | 496 | 91 | 0 | 0 | 0 | 0 |
| *Zea mays* | corn | Tx732 | 18 | >1404 | >1200 | >1020 | >191 | 49 | 33 | 16 | 11 |
| *Zea mays* | corn | Tx714 | | | | | | | | | |
| *Zea mays* | corn | Tx772 | | | | | | | | | |
| *Zea mays* subs. Mexicana | corn | PI-566673 | 19 | >2850 | >1900 | >190 | >190 | 44 | 31 | 11 | 2 |
| *Zea mays* subs. Mexicana | corn | PI-566677 | | | | | | | | | |

TABLE 6-continued

Pollen tube growth in *sorghum* wide crosses

| Species | Common | Assession | Pistils | Pollen Grains | Germination | Stigma | Axis | γ 4 | Style γ 2 | Base | Ovary |
|---|---|---|---|---|---|---|---|---|---|---|---|
| Zea mays subs. Mexicana | corn | PI-566682 | 24 | >2900 | >2857 | >1814 | 35 | 1 | 1 | 1 | 1 |
| Zea nicaraguensis | corn | PI-615697 | | | | | | | | | |
| Zea perennis | corn | Ames-21874 | | | | | | | | | |
| Zea diploperennis | corn | PI-462368 | | | | | | | | | |
| Sorghum bicolor | sorghum | B.Tx623 | | | | | | | | | |
| | | TNC/pistil = | | >150 | >150 | >100 | >10 | >10 | | | |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 2,799,241; U.S. Pat. No. 3,089,824; U.S. Pat. No. 3,177,027; U.S. Pat. No. 3,196,827; U.S. Pat. No. 3,207,824; U.S. Pat. No. 3,241,520; U.S. Pat. No. 3,253,994; U.S. Pat. No. 3,849,934; U.S. Pat. No. 4,355,108; U.S. Pat. No. 4,461,648; U.S. Pat. No. 4,535,060; U.S. Pat. No. 4,936,904; U.S. Pat. No. 5,053,231; U.S. Pat. No. 5,545,818; U.S. Pat. No. 5,602,321; U.S. Pat. No. 6,927,048.
U.S. Plant Pat. No. PP17,636; U.S. Plant Pat. No. PP18,807; U.S. Plant Pat. No. PP18,826
U.S. Pat. Publ. 20040049802; U.S. Patent Publ. 20080092255.
Bevan et al., *Nucleic Acids Research*, 11 (2):369-385, 1983.
Bouchez et al., *EMBO Journal*, 8(13):4197-4204, 1989.
Callis et al., *Genes Dev.*, 1:1183-1200, 1987.
Chandler et al., *The Plant Cell*, 1:1175-1183, 1989.
Clifton-Brown et al., In; *Miscanthus for Energy and Fibre*, Jones and Walsh (Eds.), James & James, London, 2001.
Conkling et al., *Plant Physiol.*, 93:1203-1211, 1990.
de Nettancourt, *Sexual Plant Reprod.*, 10:185-199, 1997.
Dellaporta et al., In: *Chromosome Structure and Function: Impact of New Concepts, 18th Stadler Genetics Symposium*, 11:263-282, 1988.
Ebert et al., 84:5745-5749, *Proc. Natl. Acad. Sci. USA*, 1987.
Ellis et al., *EMBO Journal*, 6(11):3203-3208, 1987.
Feng et al., *Molec. Biol. Reports*, 33:215-221, 2006.
Fromm et al., *Nature*, 319:791-793, 1986.
Gallie et al., *The Plant Cell*, 1:301-311, 1989.
Girijashankar et al., *Plant Cell Rep.*, 24, 513-522, 2005.
Hamilton et al., *Proc. Natl. Acad. Sci. USA*, 93(18):9975-9979, 1996.
Haseloff et al., *Proc. Natl. Acad. Sci. USA*, 94(6):2122-2127, 1997.
Hinchee et al., *Bio/technol.*, 6:915-922, 1988.
Hodnett et al., *Crop Science*, 45:1403-1409, 2005.
Hogenboom, *Euphytica*, 22:219-233, 1973.
Hudspeth and Grula, *Plant Mol. Biol.*, 12:579-589, 1989.
Ikuta et al., *Bio/technol.*, 8:241-242, 1990.
Islam-Faridi et al., *Genetics*, 161:345-353, 2002.
Katz et al., *J. Gen. Microbiol.*, 129:2703-2714, 1983.
Krishnaveni et al., *J. of Genetics and Breeding*, 55, 151-158, 2001.
Laurie and Bennett, *Annals Botany*, 64:675-681, 1989.
Lawton et al., *Plant Mol. Biol.* 9:315-324, 1987.
Lee et al., *Adv. Biochem. Engng. Biotech.*, 65: 93-115, 1999
Lee et al., *Korean J. Genet.*, 11(2):65-72, 1989.
Matthews et al., *J. Plant Sci.*, 163:441-450, 2002.
McClure and Franklin-Tong, *Planta*, 224:233-245, 2006.
Menz et al., *Plant Molec., Biol.*, 48:483-499, 2002.
Morjanoff and Gray, *Biotechnol. Bioeng.* 29:733-741, 1987.
Murakami et al., *Mol. Gen. Genet.*, 205:42-50, 1986.
Murashige and Skoog, *Physiol. Plant.*, 15:473-497, 1962.
Naithani et al., *Proc. Natl. Acad. Sci. USA*, 104:12211-12216, 2007.
Nasrallah and Nasrallah, *Plant Cell*, 5:1325-1335, 1993.
Nasrallah, *Science*, 296:305-308, 2002.
Odell et al., *Nature*, 313:810-812, 1985.
Ow et al., *Science*, 234:856-859, 1986.
Paterson et al., *Proc. Natl. Acad. Sci. USA*, 101:9903-9908, 2004.
PCT App. WO 97/41228
Pedersen and Toy, *Crop Science*, 37(6):1973-1975, 1997.
Potrykus et al., *Mol. Gen. Genet.*, 199:183-188, 1985.
Prasher et al., *Biochem. Biophys. Res. Commun.*, 126(3):1259-1268, 1985.
Price et al., *Crop Science*, 46:2617-2622, 2006.
Rahman et al., *Sexual Plant Reprod.*, 20:73-85, 2007.
Reichel et al., *Proc. Natl. Acad. Sci. USA*, 93: 5888-5893. 1996.
Rooney et al., *Biofuels, Bioproducts and Biorefining.*, 1: 147-157, 2007.
Sambrook et al., In: *Molecular Cloning-A Laboratory Manual* (second edition), Cold Spring Harbour Laboratory Press, 1989.
Schwarzacher et al., *Ann. Botany*, 64:315-324, 1989.
Sheen et al., *Plant Journal*, 8(5):777-784, 1995.
Stalker et al., *Science*, 242:419-422, 1988.
Sullivan et al., *Mol. Gen. Genet.*, 215(3):431-440, 1989.
Sutcliffe, *Proc. Natl. Acad. Sci. USA*, 75:3737-3741, 1978.
Swanson et al., *Ann. Rev. Genetics*, 38:793-818, 2004.
Tabah et al., *Sexual Plant Reprod.*, 17:131-140, 2004.
Thillet et al., *J. Biol. Chem.*, 263:12500-12508, 1988.
Tian, Sequin, Charest, *Plant Cell Rep.*, 16:267-271, 1997.

Twell et al., Plant Physiol 91:1270-1274, 1989.
Vasil et al., *Plant Physiol.,* 91:1575-1579, 1989.
Walker et al., *Proc. Natl. Acad. Sci. USA,* 84:6624-6628, 1987.
Wang et al., Molecular and Cellular Biology, 12(8):3399-3406, 1992.
Wheeler et al., *New Phytologist,* 151:565-584, 2001.
Yang and Russell, *Proc. Natl. Acad. Sci. USA,* 87:4144-4148, 1990.
Zhu et al., *J. Genetics and Breeding,* 52, 243-252 1998.
Zukowsky et al., *Proc. Natl. Acad. Sci. USA,* 80:1101-1105, 1983.

What is claimed is:

1. A method for producing an intergeneric hybrid embryo or seed, the method comprising crossing a sorghum parent plant with a *Saccharum* parent plant, wherein the sorghum plant is homozygous for a recessive sorghum iap allele and is used as a female parent.

2. The method of claim 1, comprising rescuing an embryo resulting from the crossing.

3. The method of claim 1, comprising growing an embryo resulting from the cross to produce an intergeneric hybrid plant.

4. The method of claim 1, wherein the embryo is comprised in a seed having a functional endosperm.

5. The method of claim 1, further comprising backcrossing the intergeneric hybrid plant, to obtain a third monocot plant.

6. The method of claim 5, further comprising inbreeding the third monocot plant to produce an introgressed progeny homozygous for at least one introgressed trait or gene.

7. The method of claim 1, wherein the sorghum parent plant comprises a gene that confers genetic or cytoplasmic male sterility.

8. The method of claim 7, wherein the sorghum parent plant is a plant of sorghum line Tx3361.

9. The method of claim 1, wherein the *Saccharum* parent plant is a *Saccharum officinarum, Saccharum spontaneum* or a *Saccharum officinarum*×*Saccharum spontaneum* hybrid plant.

10. The method of claim 1, wherein crossing a sorghum parent plant with a *Saccharum* parent plant comprises:
    (i) collecting pollen from the *Saccharum* parent plant; and
    (ii) pollinating a flower on the sorghum parent plant with said pollen.

11. The method of claim 1, wherein the intergeneric hybrid plant or seed is treated with a chromosome-doubling agent.

12. The method of claim 11, wherein the chromosome-doubling agent is a chemical chromosome doubling agent.

* * * * *